US011259798B2

(12) United States Patent
Limon et al.

(10) Patent No.: US 11,259,798 B2
(45) Date of Patent: Mar. 1, 2022

(54) MEDICAL DEVICES HAVING TISSUE GRASPING SURFACES AND FEATURES FOR MANIPULATING SURGICAL NEEDLES

(71) Applicant: Intuitive Surgical Operations, Inc., Sunnyvale, CA (US)

(72) Inventors: Timothy A. Limon, Cupertino, CA (US); Grant Duque, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 51 days.

(21) Appl. No.: 16/511,545

(22) Filed: Jul. 15, 2019

(65) Prior Publication Data
US 2020/0015807 A1 Jan. 16, 2020

Related U.S. Application Data
(60) Provisional application No. 62/698,434, filed on Jul. 16, 2018.

(51) Int. Cl.
*A61B 17/062* (2006.01)
*A61B 34/30* (2016.01)
*A61B 17/28* (2006.01)

(52) U.S. Cl.
CPC .......... *A61B 17/062* (2013.01); *A61B 17/282* (2013.01); *A61B 34/30* (2016.02)

(58) Field of Classification Search
CPC . A61B 17/062; A61B 17/282; A61B 17/0469; A61B 17/0625;
(Continued)

(56) References Cited

U.S. PATENT DOCUMENTS 4,165,745 A 8/1979 Heifetz
5,052,402 A 10/1991 Bencini et al.
(Continued)

FOREIGN PATENT DOCUMENTS

CN 1939228 A 4/2007
CN 101045015 A 10/2007
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Kathleen S Holwerda
*Assistant Examiner* — Lauren Dubose

(57) ABSTRACT

A medical device includes a clevis, a first jaw, and a second jaw. The first jaw includes a first proximal gripping portion and a first distal gripping portion, and the first proximal gripping portion includes a first needle alignment portion. The second jaw is coupled to the clevis and includes a second proximal gripping portion and a second distal gripping portion, and the second proximal gripping portion includes a second needle alignment portion. The first and second needle alignment portions are located opposite each other when in the closed orientation. The first and second needle alignment portions define a clamp path when in the closed orientation within which the curved portion of the needle is received when the second jaw is in the open orientation. The first and second needle alignment portions are configured to rotate the needle when moving to the closed orientation.

4 Claims, 23 Drawing Sheets

(58) Field of Classification Search
CPC ...... A61B 2017/2926; A61B 17/06061; A61B 17/28; A61B 17/29
USPC ........................................................ 606/147
See application file for complete search history.

(56) References Cited

U.S. PATENT DOCUMENTS

| | | | |
|---|---|---|---|
| 5,257,999 A * | 11/1993 | Slanetz, Jr. | A61B 17/0469 606/147 |
| 5,318,589 A | 6/1994 | Lichtman | |
| 5,373,854 A | 12/1994 | Kolozsi | |
| 5,395,375 A | 3/1995 | Turkel et al. | |
| 5,396,900 A | 3/1995 | Slater et al. | |
| 5,476,479 A | 12/1995 | Green et al. | |
| 5,482,054 A | 1/1996 | Slater et al. | |
| 5,496,317 A | 3/1996 | Goble et al. | |
| 5,496,347 A | 3/1996 | Hashiguchi et al. | |
| 5,527,339 A | 6/1996 | Koscher et al. | |
| 5,575,805 A | 11/1996 | Li | |
| 5,582,617 A | 12/1996 | Klieman et al. | |
| 5,601,575 A | 2/1997 | Measamer et al. | |
| 5,792,165 A | 8/1998 | Klieman et al. | |
| 5,855,583 A | 1/1999 | Wang et al. | |
| 5,906,630 A | 5/1999 | Anderhub et al. | |
| 5,968,074 A | 10/1999 | Prestel | |
| 6,206,903 B1 | 3/2001 | Ramans | |
| 6,214,010 B1 | 4/2001 | Farley et al. | |
| 6,273,860 B1 | 8/2001 | Kostylev et al. | |
| 6,331,181 B1 | 12/2001 | Tierney et al. | |
| 6,368,290 B1 | 4/2002 | Baska | |
| 6,394,998 B1 | 5/2002 | Wallace et al. | |
| 6,491,691 B1 | 12/2002 | Morley et al. | |
| 6,554,844 B2 | 4/2003 | Lee et al. | |
| 6,582,451 B1 | 6/2003 | Marucci et al. | |
| 6,623,482 B2 | 9/2003 | Pendekanti et al. | |
| 6,663,641 B1 | 12/2003 | Kovac et al. | |
| 6,685,698 B2 | 2/2004 | Morley et al. | |
| 6,817,974 B2 | 11/2004 | Cooper et al. | |
| 6,840,938 B1 | 1/2005 | Morley et al. | |
| 6,843,793 B2 | 1/2005 | Brock et al. | |
| 6,949,106 B2 | 9/2005 | Brock et al. | |
| 6,994,708 B2 | 2/2006 | Manzo et al. | |
| 7,083,571 B2 | 8/2006 | Wang et al. | |
| 7,090,683 B2 | 8/2006 | Brock et al. | |
| 7,147,650 B2 | 12/2006 | Lee | |
| 7,169,141 B2 | 1/2007 | Brock et al. | |
| 7,214,230 B2 | 5/2007 | Brock et al. | |
| 7,338,513 B2 | 3/2008 | Lee et al. | |
| 7,371,210 B2 | 5/2008 | Brock et al. | |
| 7,608,083 B2 | 10/2009 | Lee et al. | |
| 7,824,401 B2 | 11/2010 | Manzo et al. | |
| 7,935,130 B2 | 5/2011 | Williams et al. | |
| 8,123,764 B2 | 2/2012 | Meade et al. | |
| 8,257,371 B2 | 9/2012 | Hamilton et al. | |
| 8,479,969 B2 | 7/2013 | Shelton, IV et al. | |
| 8,602,288 B2 | 12/2013 | Shelton, IV et al. | |
| 8,800,838 B2 | 8/2014 | Shelton, IV et al. | |
| 9,028,494 B2 | 5/2015 | Shelton, IV et al. | |
| 9,078,684 B2 | 7/2015 | Williams et al. | |
| 9,113,861 B2 * | 8/2015 | Martin | A61B 17/062 |
| 9,204,923 B2 | 12/2015 | Manzo et al. | |
| 9,339,341 B2 | 5/2016 | Cooper | |
| 9,358,031 B2 | 6/2016 | Manzo et al. | |
| 9,456,839 B2 | 10/2016 | Cooper et al. | |
| 9,615,846 B2 | 4/2017 | Prestel | |
| 9,844,369 B2 | 12/2017 | Huitema et al. | |
| 9,918,731 B2 | 3/2018 | Cooper et al. | |
| 10,130,366 B2 | 11/2018 | Shelton, IV et al. | |
| 10,667,873 B2 | 6/2020 | Wallace | |
| 2004/0260198 A1 | 12/2004 | Rothberg et al. | |
| 2005/0187547 A1 | 8/2005 | Sugi | |
| 2006/0074415 A1 | 4/2006 | Scott et al. | |
| 2006/0184198 A1 | 8/2006 | Bales et al. | |
| 2007/0208375 A1 | 9/2007 | Nishizawa et al. | |
| 2008/0046122 A1 | 2/2008 | Manzo et al. | |
| 2008/0065102 A1 | 3/2008 | Cooper et al. | |
| 2008/0065105 A1 | 3/2008 | Larkin et al. | |
| 2008/0125794 A1 | 5/2008 | Brock et al. | |
| 2008/0196533 A1 | 8/2008 | Bergamasco et al. | |
| 2009/0088774 A1 | 4/2009 | Swarup et al. | |
| 2009/0110533 A1 | 4/2009 | Jinno et al. | |
| 2009/0131975 A1 | 5/2009 | Ahlberg et al. | |
| 2009/0198272 A1 | 8/2009 | Kerver et al. | |
| 2009/0326530 A1 | 12/2009 | Orban, III et al. | |
| 2010/0030238 A1 | 2/2010 | Viola et al. | |
| 2011/0295269 A1 | 12/2011 | Swensgard et al. | |
| 2011/0295270 A1 | 12/2011 | Giordano et al. | |
| 2012/0116433 A1 | 5/2012 | Houser et al. | |
| 2012/0289975 A1 | 11/2012 | Martin et al. | |
| 2012/0316580 A1 * | 12/2012 | Belman | A61B 17/062 606/145 |
| 2013/0144395 A1 | 6/2013 | Stefanchik et al. | |
| 2014/0005662 A1 * | 1/2014 | Shelton, IV | A61B 34/30 606/41 |
| 2014/0005678 A1 | 1/2014 | Shelton, IV et al. | |
| 2014/0005708 A1 | 1/2014 | Shelton, IV | |
| 2014/0100558 A1 | 4/2014 | Schmitz et al. | |
| 2014/0243850 A1 | 8/2014 | Sadaka | |
| 2014/0276956 A1 | 9/2014 | Crainich et al. | |
| 2015/0150635 A1 | 6/2015 | Kilroy et al. | |
| 2015/0157355 A1 | 6/2015 | Price et al. | |
| 2015/0313676 A1 | 11/2015 | Deodhar | |
| 2016/0000423 A1 * | 1/2016 | Shields | A61B 17/062 606/147 |
| 2016/0287279 A1 | 10/2016 | Bovay et al. | |
| 2016/0303743 A1 | 10/2016 | Rockrohr et al. | |
| 2017/0165017 A1 | 6/2017 | Chaplin et al. | |
| 2017/0333037 A1 | 11/2017 | Wellman et al. | |
| 2018/0168572 A1 | 6/2018 | Burbank | |
| 2018/0206904 A1 | 7/2018 | Felder | |
| 2019/0099227 A1 | 4/2019 | Rockrohr | |
| 2019/0192137 A1 | 6/2019 | Shelton, IV et al. | |
| 2019/0223960 A1 | 7/2019 | Chaplin et al. | |
| 2019/0231374 A1 | 8/2019 | Kimura et al. | |
| 2019/0374297 A1 | 12/2019 | Wallace et al. | |
| 2020/0022765 A1 | 1/2020 | Limon et al. | |
| 2020/0054405 A1 | 2/2020 | Schuh et al. | |
| 2020/0054408 A1 | 2/2020 | Schuh et al. | |
| 2020/0138531 A1 | 5/2020 | Chaplin | |
| 2020/0155136 A1 | 5/2020 | Shuh et al. | |
| 2020/0155253 A1 | 5/2020 | Shuh et al. | |
| 2020/0261104 A1 * | 8/2020 | Jogasaki | A61B 17/29 |

FOREIGN PATENT DOCUMENTS

| | | |
|---|---|---|
| WO | WO-2011161626 A2 | 12/2011 |
| WO | WO-2012068156 A2 | 5/2012 |
| WO | WO-2014025204 A1 | 2/2014 |
| WO | WO-2016025132 A1 | 2/2016 |
| WO | WO-2016045041 A1 | 3/2016 |
| WO | WO-2017064303 A1 | 4/2017 |
| WO | WO-2017189272 A1 | 11/2017 |
| WO | WO-2018069679 A1 | 4/2018 |

* cited by examiner

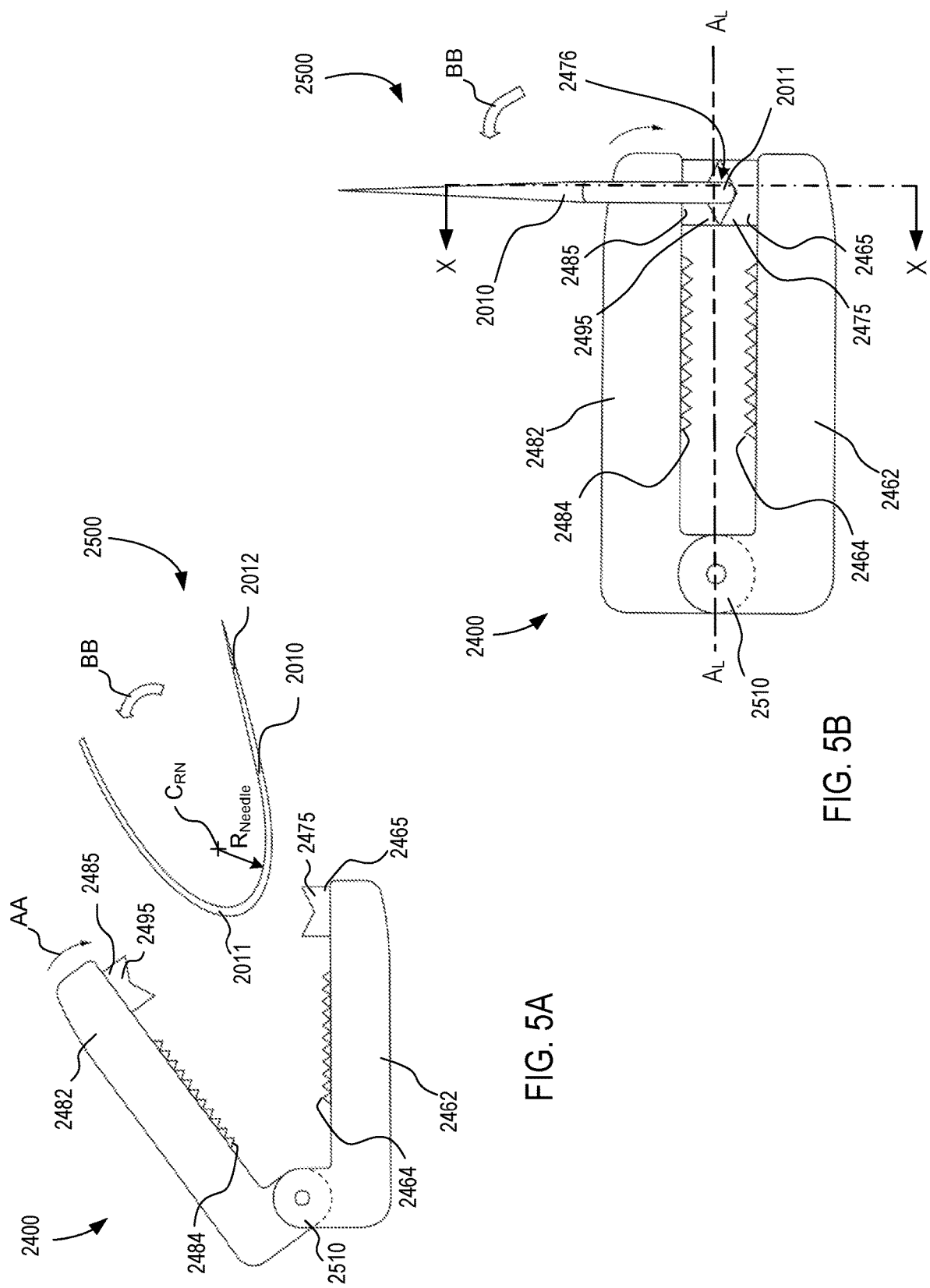

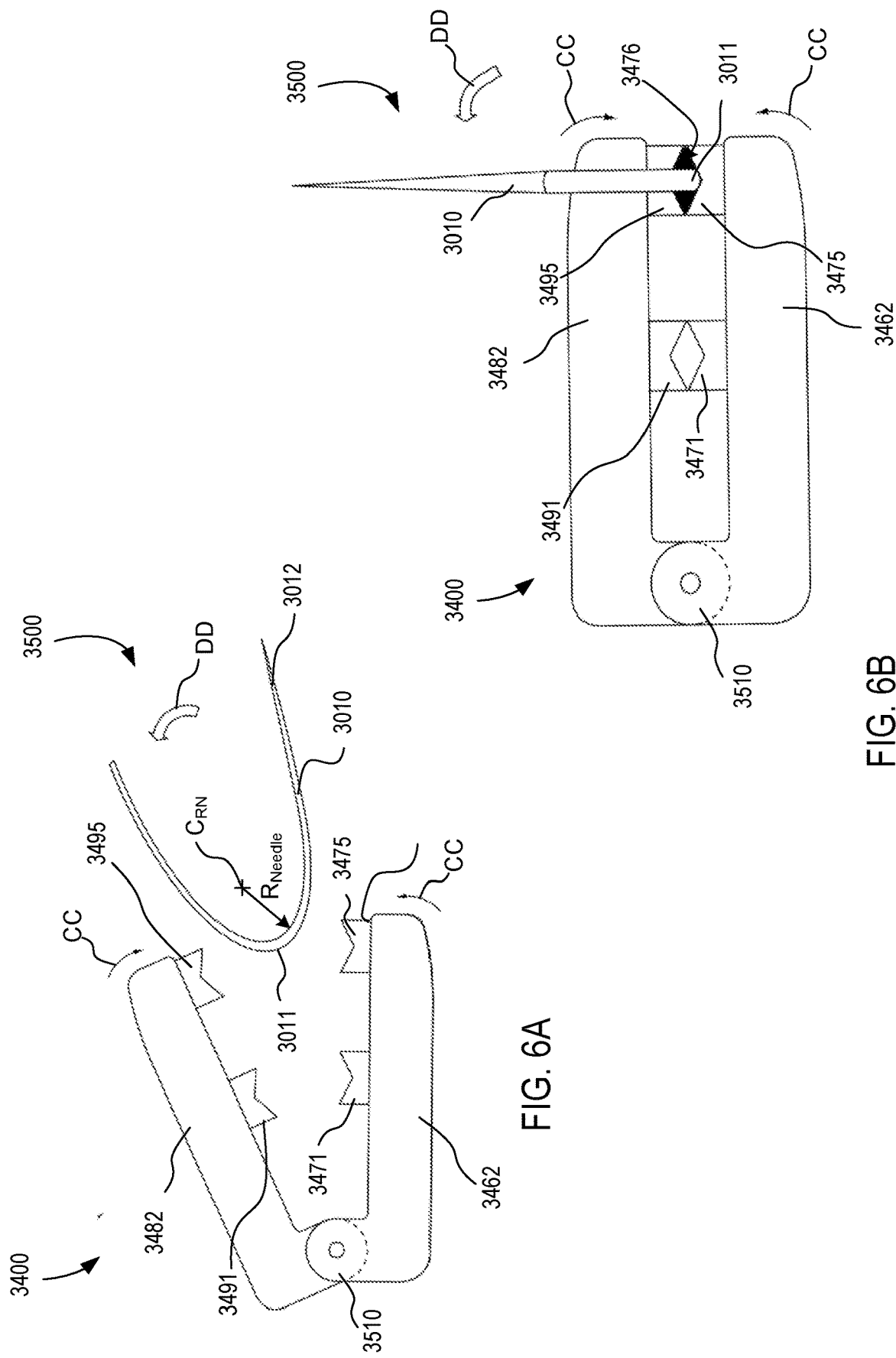

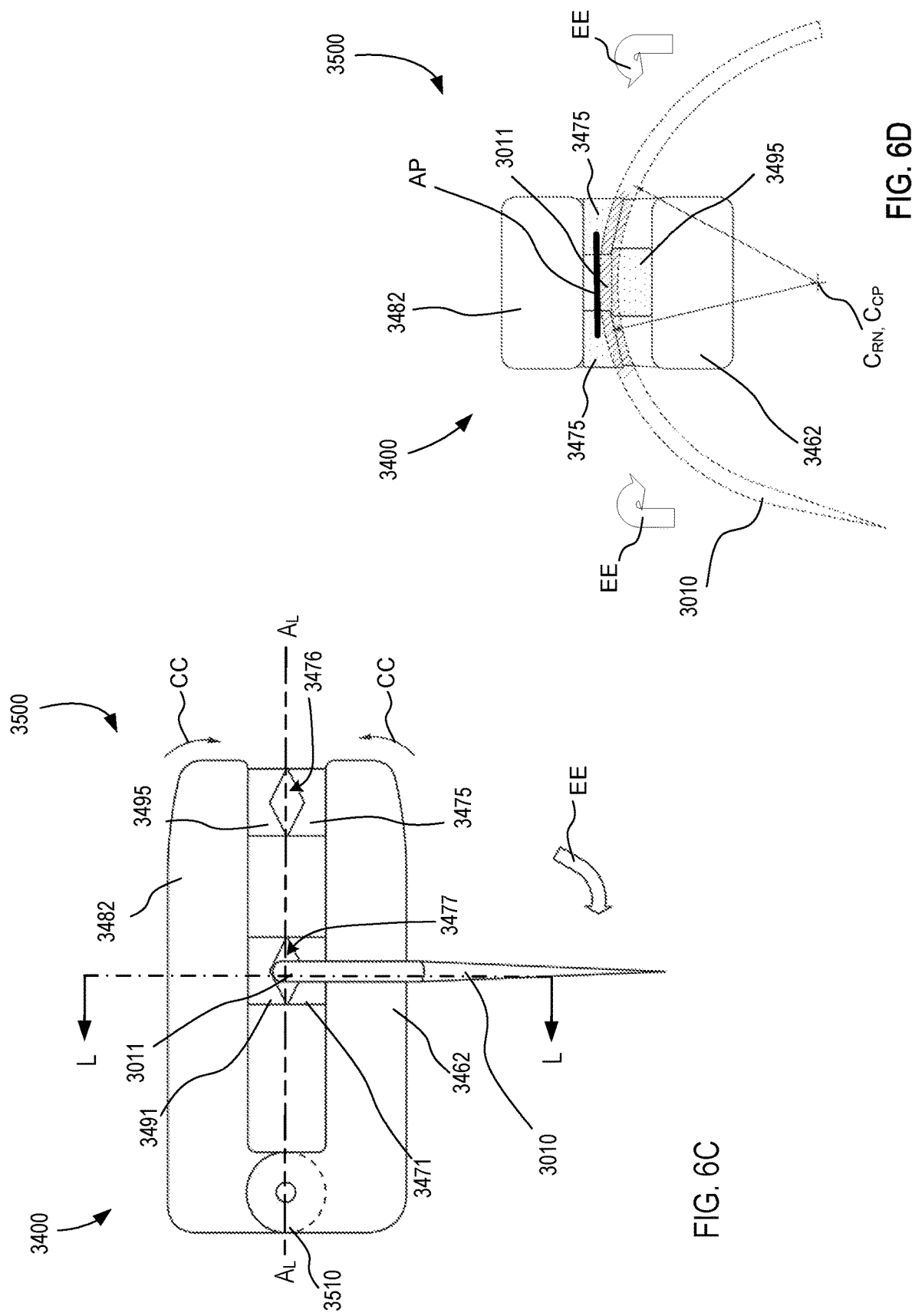

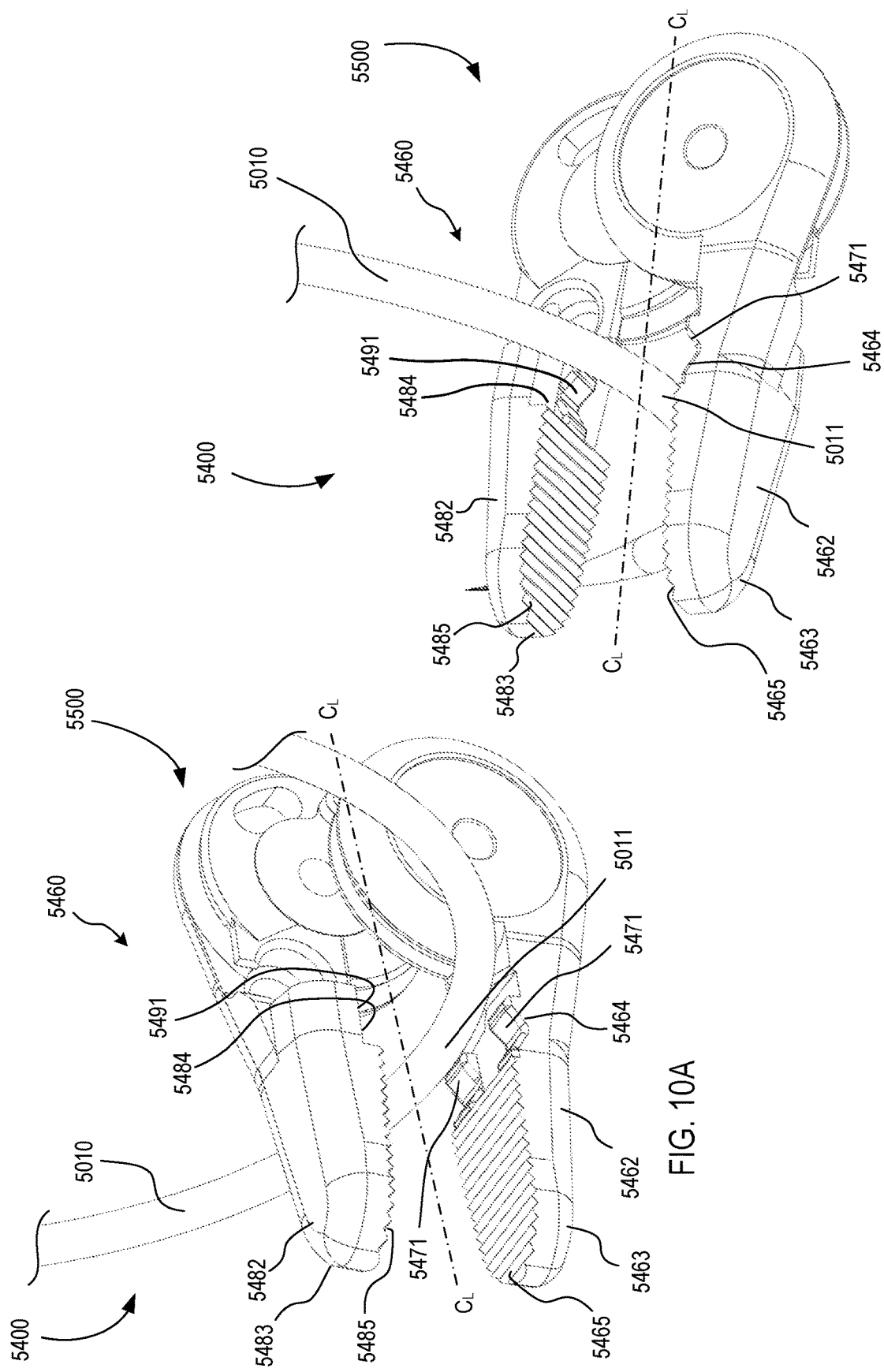

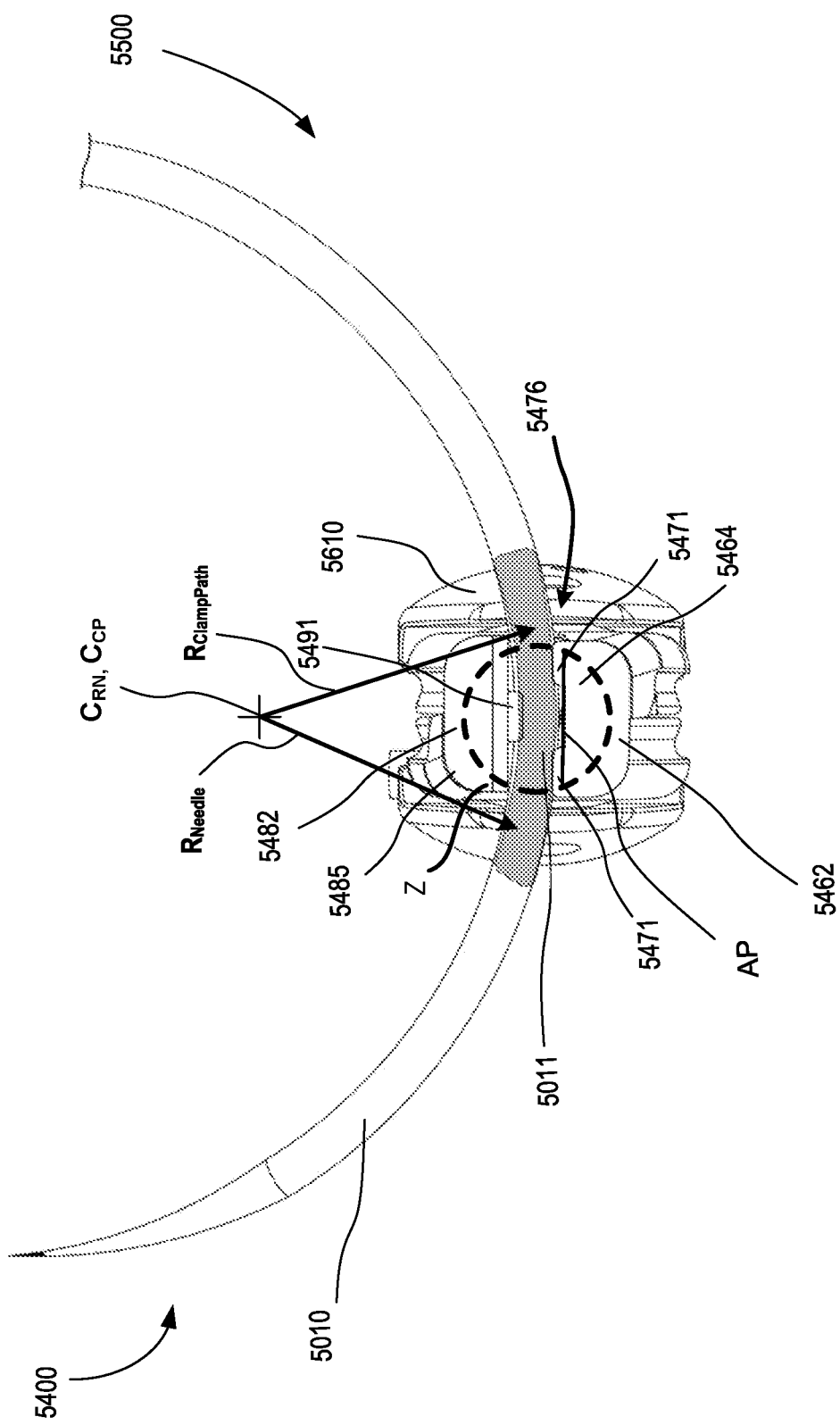

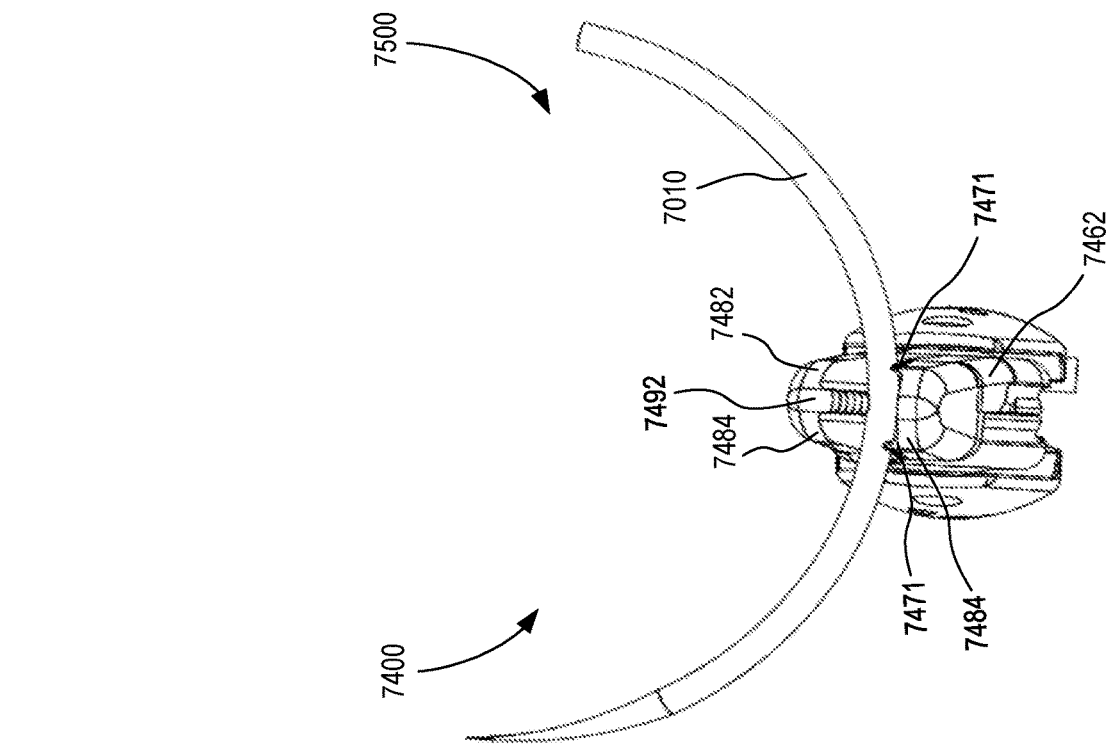
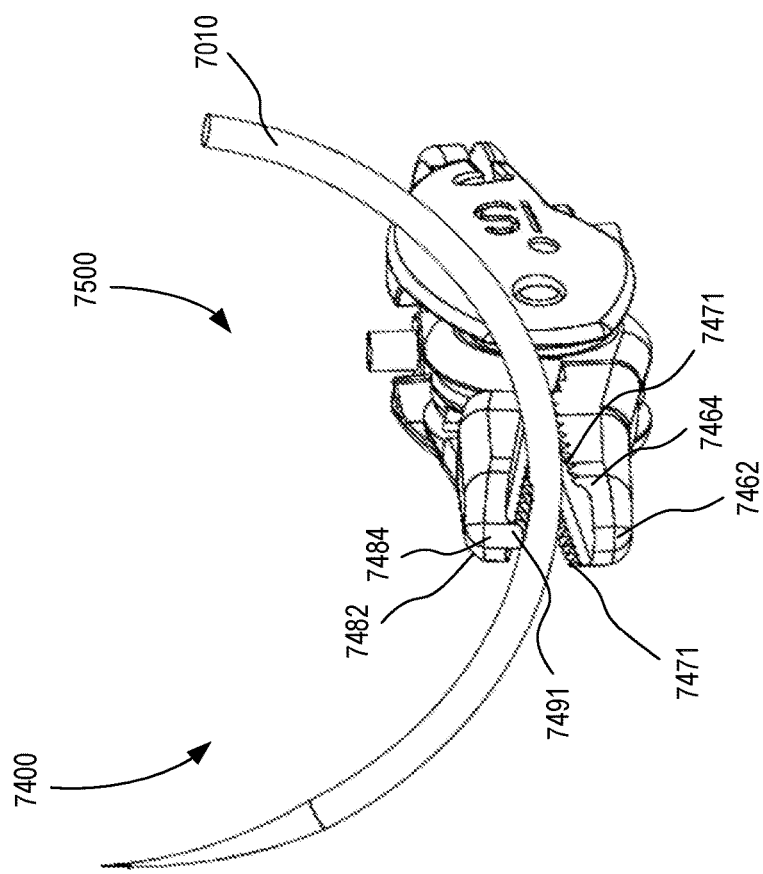

MEDICAL DEVICES HAVING TISSUE GRASPING SURFACES AND FEATURES FOR MANIPULATING SURGICAL NEEDLES

CROSS-REFERENCE TO RELATED APPLICATIONS

This patent application claims priority to and the filing date benefit of U.S. Provisional Application No. 62/698,434 (filed Jul. 16, 2018)(entitled "Medical Devices Having Tissue Grasping Surfaces and Features for Manipulating Surgical Needles"), which is incorporated herein by reference in its entirety.

BACKGROUND

The embodiments described herein relate to grasping tools, more specifically to medical devices, and still more specifically to endoscopic tools. More particularly, the embodiments described herein relate to medical devices that include jaws having a self-righting needle alignment portion that can be used, for example, in surgical applications.

Known techniques for Minimally Invasive Surgery (MIS) employ instruments to manipulate tissue that can be either manually controlled or controlled via computer-assisted teleoperation. Many known MIS instruments include a therapeutic or diagnostic end effector (e.g., forceps, a cutting tool, or a cauterizing tool) mounted on a wrist mechanism at the distal end of an extension (also referred to herein as the main tube or shaft). During an MIS procedure, the end effector, wrist mechanism, and the distal end of the main tube can be inserted into a small incision or a natural orifice of a patient to position the end effector at a work site within the patient's body. The optional wrist mechanism can be used to change the end effector's orientation with respect to the main tube to perform the desired procedure at the work site. Known wrist mechanisms generally provide the desired degrees of freedom (DOFs) for movement of the end effector. For example, for forceps or other grasping tools, known wrist mechanisms are often able to change the pitch and yaw of the end effector with reference to the main tube. A wrist may optionally provide a roll DOF for the end effector, or the roll DOF may be implemented by rolling the main tube. An end effector may optionally have additional mechanical DOFs, such as grip or knife blade motion. In some instances, wrist and end effector mechanical DOFs may be combined. For example, U.S. Pat. No. 5,792,135 (filed May 16, 1997) discloses a mechanism in which wrist and end effector grip DOFs are combined.

To enable the desired movement of the wrist mechanism and end effector, known instruments include tension members (e.g., cables, cable/hypotube combinations, tension bands) that extend through the main tube of the instrument and that connect the wrist mechanism to a transmission or actuator (also referred to herein as a backend mechanism). The backend mechanism moves the cables to operate the wrist mechanism. For computer-assisted systems, the backend mechanism is motor driven and can be operably coupled to a processing system to provide a user interface for a doctor to control the instrument.

Patients benefit from continual efforts to improve the effectiveness of MIS methods and tools. For example, reducing the size and/or the operating footprint of the main tube and wrist mechanism can allow for smaller entry incisions, thereby reducing the negative effects of surgery, such as pain, scarring, and undesirable healing time. But, producing small diameter medical instruments that implement the clinically desired functions for minimally invasive procedures can be challenging. Specifically, simply reducing the size of known wrist mechanisms by "scaling down" the components will not result in an effective solution because required component and material properties do not scale.

Another way to reduce the negative effects of surgery is to minimize the number of times that the wrist mechanism or end effector is moved into and out of the operation area of the patient. For example, some medical instruments have end effectors with gripping jaws coupled to the wrist mechanism, which can be used for performing clinical functions including cutting, dissection, incising, cauterizing, destroying tissue, and suturing. Such known medical instruments have an opposing set of jaws that can be operated to contact tissue and interact with other medical instruments. Some instruments include jaws that can grip a surgical needle therebetween and manipulate the needle to perform suturing functions. However, it can be difficult to orient the needle between the jaws of these instruments at a desired orientation for suturing. Further, it can be challenging to maintain the orientation of the needle when gripped between the jaws and while maneuvering the needle under surgical conditions, such as while maneuvering the needle within a small operating area and within a lubricious environment. Moreover, these conventional instruments are typically withdrawn from the clinical operations area during use by the operator to switch instruments (e.g., between a tissue gripping instrument and a suturing instrument) or modify the needle orientation according to surgical needs and conditions, so as to avoid the high risk of the needle slipping during such adjustments. Such manipulations can slow the suturing process and increase related challenges for maintaining a sterile clinical environment.

Thus, a need exists for improved endoscopic tools including tools for performing suturing clinical functions. Improvements may include wrist mechanisms having jaws with one or more gripping portions providing enhanced retention of surgical needles for suturing, and improved flexibility for quickly changing or modifying the needle orientation during use.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter.

A medical device includes a clevis, a first jaw, and a second jaw. The first jaw is coupled to the clevis and has a first gripping portion and a second gripping portion. The second gripping portion includes a first needle alignment portion and the first gripping portion is configured to engage a target tissue. The second jaw is coupled to the clevis and has a third gripping portion and a fourth gripping portion. The fourth gripping portion includes a second needle alignment portion and the third gripping portion is configured to engage the target tissue. The second jaw is movable with respect to the first jaw between an open orientation and a closed orientation. The second needle alignment portion is located opposite and aligned with the first needle alignment portion when the second jaw is in the closed orientation. The first needle alignment portion and the second needle alignment portion are configured to receive a curved portion of a needle between the first needle alignment portion and the second needle alignment portion when the second jaw is in the open orientation. The first and second needle alignment portions define a clamp path within which the curved portion of the needle is received when the second jaw is in the closed orientation. The clamp path has a radius of curvature corresponding with a radius of the curved portion of the needle, and a center of the radius of curvature is located at a pre-determined orientation with respect to the first and second jaws.

In some embodiments, the first and the second needle alignment portions are configured to rotate the needle by clamping the curved portion of the needle when the second jaw moves from the open orientation to the closed orientation such that the curved portion of the needle aligns with the radius of curvature of the clamp path. In some embodiments, the pre-determined orientation includes an upward orientation in which the center of the radius of curvature is located on an opposite side of the second jaw from the first jaw when the second jaw is in the closed orientation. In some embodiments, the pre-determined orientation includes a downward orientation in which the center of the radius of curvature is located on a same side of the second jaw as the first jaw when the second jaw is in the closed orientation.

In some embodiments, the clamp path is a first clamp path, the radius of curvature is a first radius of curvature, the pre-determined orientation is a first pre-determined orientation, the first gripping portion includes a third needle alignment portion, the third gripping portion includes a fourth needle alignment portion, and the third needle alignment portion and the fourth needle alignment portion are configured to receive the curved portion of the needle when the second jaw is in the open orientation. The third and fourth gripping portions define a second clamp path within which the curved portion of the needle is received when the second jaw is in the closed orientation. The second clamp path has a second radius of curvature corresponding with the radius of the curved portion of the needle, and a center of the second radius of curvature is located at a second pre-determined orientation with respect to the first and second jaws.

In some embodiments, the first needle alignment portion includes a pair of first clamp supports extending toward the second needle alignment portion when in the closed orientation. The pair of first clamp supports are laterally spaced apart on the first jaw with respect to a longitudinal axis of the first and second jaws when the second jaw is in the closed orientation. The second needle alignment portion includes a second clamp support extending toward the first needle alignment portion when in the closed orientation. The second clamp support is located along the longitudinal axis of the first and the second jaws when in the closed orientation. The second clamp support and the pair of first clamp supports define the clamp path when the second jaw is in the closed orientation.

In some embodiments, the first needle alignment portion and the second needle alignment portion are located at proximal portions of the first and the second jaws. The first needle alignment portion of the first jaw includes a first proximal needle alignment portion and the second needle alignment portion of the second jaw includes a second proximal needle alignment portion. The second gripping portion and the fourth gripping portions are located at distal portions of the first and the second jaws. The second gripping portion includes a first distal needle alignment portion, and the fourth gripping portion includes a second distal needle alignment portion. The first and second proximal needle alignment portions are located opposite and aligned with each other when the first and the second jaw are in the closed orientation. The first and second distal needle alignment portions are located opposite and aligned with each other when the first and the second jaw are in the closed orientation. The first and second proximal needle alignment portions are configured to retain the needle in a proximal orientation when in the closed orientation. The first and second distal needle alignment portions are configured to retain the needle in a distal orientation when in the closed orientation.

In some embodiments, an apparatus includes a clevis, a first jaw, and a second jaw. The first jaw is coupled to the clevis and has a proximal end portion, a distal end portion, and a first needle alignment portion located between the proximal end portion and the distal end portion. The first needle alignment portion includes a first clamp support. The second jaw is coupled to the clevis and has a proximal end portion, a distal end portion, and a second needle alignment portion located between the proximal and distal end portion of the second jaw. The second needle alignment portion includes a second clamp support and is movable with respect to the first jaw between an open orientation and a closed orientation. The first and the second jaws define a longitudinal axis when the second jaw is in the closed orientation. The first and the second clamp supports extend toward each other when the second jaw is in the closed orientation. The second clamp support is located opposite and distally offset from first clamp support along the longitudinal axis when the second jaw is in the closed orientation. The first clamp support and the second clamp support define a clamp path within which a curved portion of a needle is received when the second jaw is in the closed orientation. The clamp path defines a needle orientation plane that intersects the longitudinal axis. The needle orientation plane is non-perpendicular with respect to the longitudinal axis when the second jaw is in the closed orientation.

Other medical devices, related components, medical device systems, and/or methods according to embodiments will be or become apparent to one with skill in the art upon review of the following drawings and detailed description. It is intended that all such additional medical devices, related components, medical device systems, and/or methods included within this description be within the scope of this disclosure.

BRIEF DESCRIPTION OF THE DRAWINGS

FIG. 5A is a diagrammatic side view of a portion of an instrument of a surgery system shown in an open orientation, according to an embodiment.

FIG. 5B is a diagrammatic side view of the portion of the instrument of FIG. 5A shown in a closed orientation.

FIG. 6A is a diagrammatic side view of a portion of an instrument of a surgery system shown in an open orientation, according to an embodiment.

FIG. 6B is a diagrammatic side view of the portion of the instrument of FIG. 6A shown in a first closed orientation with a needle clamped at a distal portion of the instrument.

FIG. 6C is a diagrammatic side view of the portion of the instrument of FIG. 6A shown in a second closed orientation with a needle clamped at a proximal portion of the instrument.

FIG. 6D is a diagrammatic cross-sectional end view of the portion of the instrument of FIG. 6C in the second closed orientation viewed from line L-L shown in FIG. 6C.

FIGS. 10A and 10B are perspective views of the distal end portion of the instrument of FIGS. 9A-9C, shown in exploded views.

FIG. 11A is a cross-sectional view of the distal end portion of FIG. 9A as viewed from line Y-Y shown in FIG. 9A.

FIGS. 16A and 16B are perspective views of the distal end portion of the instrument of FIG. 15.

DETAILED DESCRIPTION

Figure 1:
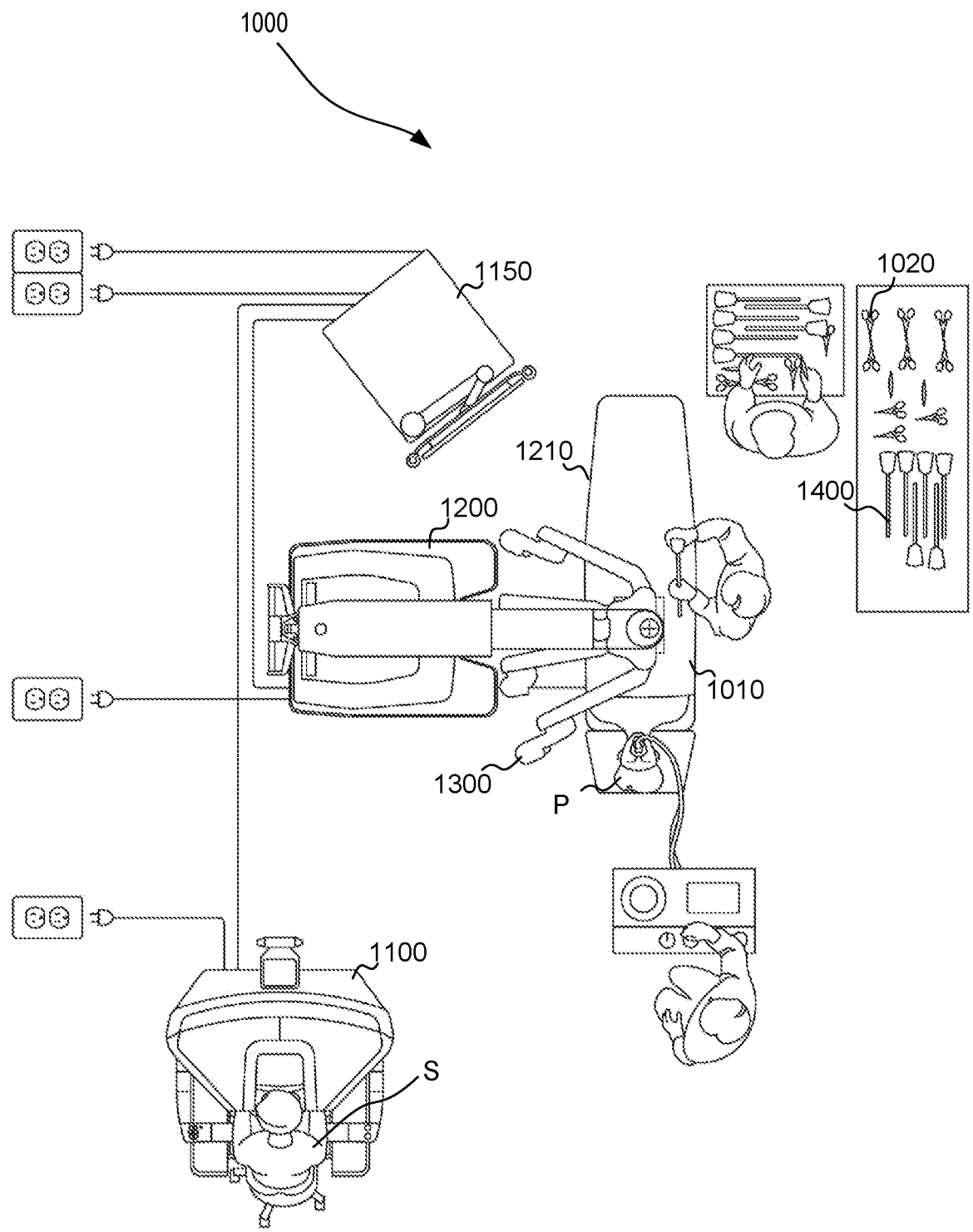
FIG. 1 is a plan view of a minimally invasive teleoperated medical system according to an embodiment, being used to perform a medical procedure such as surgery.

The embodiments described herein can advantageously be used in a wide variety of grasping, cutting, manipulating, and suturing surgical operations associated with minimally invasive surgery. In particular, the instruments described herein can be low-cost, disposable instruments that facilitate being used for only one clinical event and/or one or more particular functions procedures during the clinical event. As described herein, the instruments include a pair of jaws having a gripping portion on each jaw. The gripping portions can be configured to engage a target tissue. Moreover, each of the gripping portions can include a needle alignment portion configured to receive a curved portion of a needle therebetween when the jaws are in an open orientation, as well as to clamp the needle when the jaws are in the closed orientation to maintain the needle in a pre-determined orientation.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

The term "flexible" in association with a part, such as a mechanical structure, component, or component assembly, should be broadly construed. In essence, the term means the part can be repeatedly bent and restored to an original shape without harm to the part. Certain flexible components can also be resilient. For example, a component (e.g., a flexure) is said to be resilient if it possesses the ability to absorb energy when it is deformed elastically, and then release the stored energy upon unloading (i.e., returning to its original state). Many "rigid" objects have a slight inherent resilient "bendiness" due to material properties, although such objects are not considered "flexible" as the term is used herein.

A flexible part may have infinite degrees of freedom (DOF's). Flexibility is an extensive property of the object being described, and thus is dependent upon the material from which the object is formed as well as certain physical characteristics of the object (e.g., cross-sectional shape, length, boundary conditions, etc.). For example, the flexibility of an object can be increased or decreased by selectively including in the object a material having a desired modulus of elasticity, flexural modulus, and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the flexibility of the object can be decreased, for example, by introducing into the object and/or constructing the object of a material having a relatively high modulus of elasticity. Examples of such parts include closed, bendable tubes (made from, e.g., NITINOL®, polymer, soft rubber, and the like), helical coil springs, etc. that can be bent into various simple or compound curves, often without significant cross-sectional deformation.

Other flexible parts may approximate such an infinite-DOF part by using a series of closely spaced components that are similar to a serial arrangement of short, connected links as snake-like "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOFs of relative movement between the links. A short, flexible part may serve as, and be modeled as, a single mechanical constraint (a joint) that provides one or more DOF's between two links in a kinematic chain, even though the flexible part itself may be a kinematic chain made of several coupled links having multiple DOFs, or an infinite-DOF link.

As used herein, the word "clamp path" refers to path for the curved portion of the needle that is defined by the needle alignment portions of the jaws when the jaws are in the closed orientation.

As used herein, the word "distal" refers to direction towards a work site, and the word "proximal" refers to a direction away from the work site. Thus, for example, the end of a tool that is closest to the target tissue would be the distal end of the tool, and the end opposite the distal end (i.e., the end manipulated by the user or coupled to the actuation shaft) would be the proximal end of the tool.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures were turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, medical device, instrument, and variants thereof, can be interchangeably used.

Aspects of the invention are described primarily in terms of an implementation using a da Vinci® Surgical System, commercialized by Intuitive Surgical, Inc. of Sunnyvale, Calif. Examples of such surgical systems are the da Vinci Xi® Surgical System (Model IS4000) and the da Vinci Si® Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are merely presented as examples, and they are not to be considered as limiting the scope of the inventive aspects disclosed herein. As applicable, inventive aspects may be embodied and implemented in both relatively smaller, hand-held, hand-operated devices and relatively larger systems that have additional mechanical support.

FIG. 1 is a plan view illustration of a computer-assisted teleoperation system. Shown is a medical device, which is a Minimally Invasive Robotic Surgical (MIRS) system 1000 (also referred to herein as a minimally invasive teleoperated surgery system), used for performing a minimally invasive diagnostic or surgical procedure on a Patient P who is lying on an Operating table 1010. The system can have any number of components, such as a user control unit 1100 for use by a surgeon or other skilled clinician S during the procedure. The MIRS system 1000 can further include a manipulator unit 1200 (popularly referred to as a surgical robot), and an optional auxiliary equipment unit 1150. The manipulator unit 1200 can include an arm assembly 1300 and a tool assembly removably coupled to the arm assembly. The manipulator unit 1200 can manipulate at least one removably coupled tool assembly 1400 (also referred to herein as a "tool") through a minimally invasive incision in the body or natural orifice of the patient P while the surgeon S views the surgical site and controls movement of the tool 1400 through control unit 1100.

An image of the surgical site is obtained by an endoscope (not shown), such as a stereoscopic endoscope, which can be manipulated by the manipulator unit 1200 to orient the endoscope. The auxiliary equipment unit 1150 can be used to process the images of the surgical site for subsequent display to the Surgeon S through the user control unit 1100. The number of tools 1400 used at one time will generally depend on the diagnostic or surgical procedure and the space constraints within the operating room, among other factors. If it is necessary to change one or more of the instruments 1400 being used during a procedure, an assistant removes the instrument 1400 from the manipulator unit 1200 and replaces it with another instrument 1400 from a tray 1020 in the operating room. Although shown as being used with the instruments 1400, any of the instruments described herein can be used with the MIRS 1000.

Figure 2:
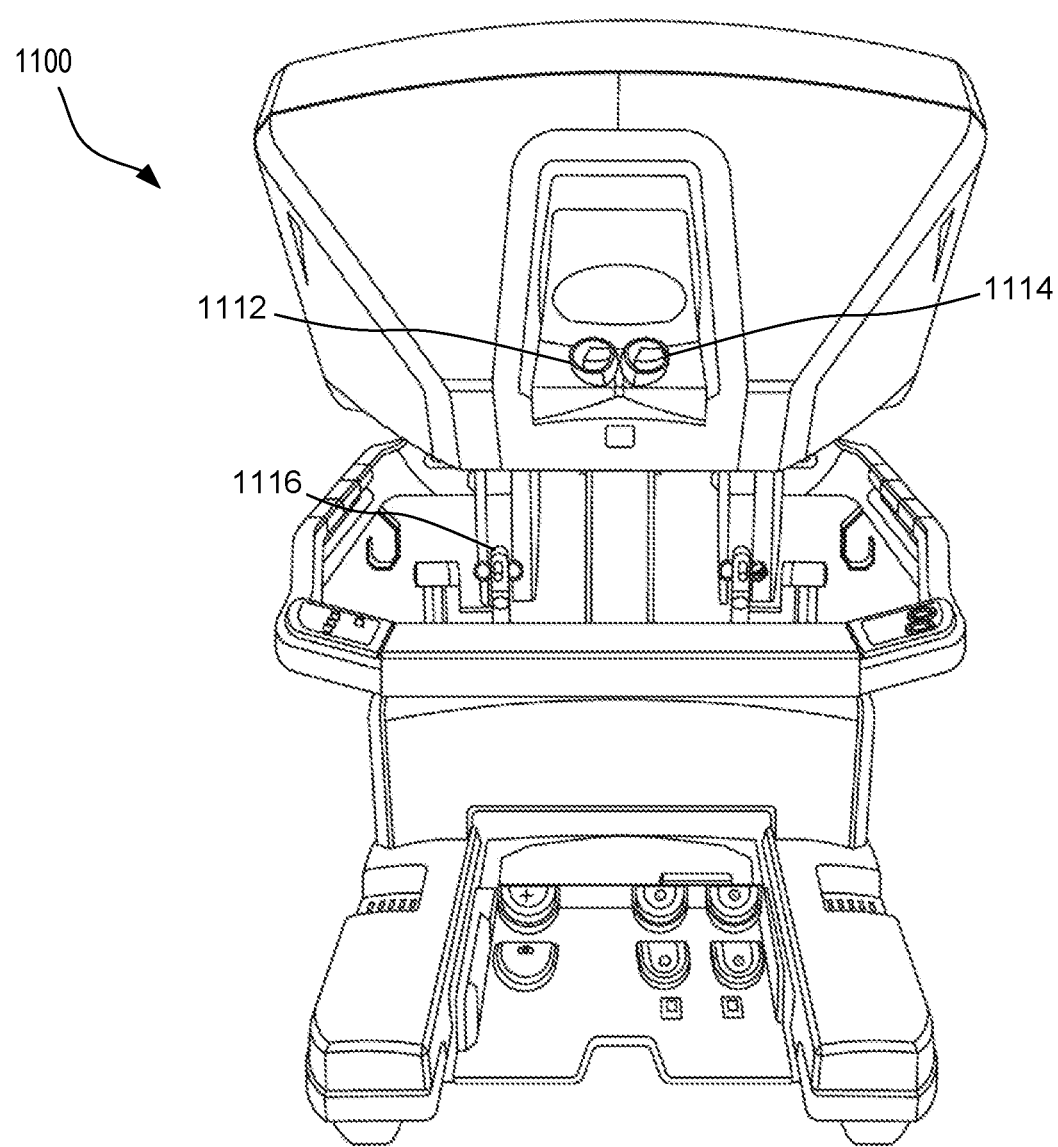
FIG. 2 is a perspective view of an optional auxiliary unit of the minimally invasive tele-operated surgery system shown in FIG. 1.

FIG. 2 is a perspective view of the control unit 1100. The user control unit 1100 includes a left eye display 1112 and a right eye display 1114 for presenting the surgeon S with a coordinated stereo view of the surgical site that enables depth perception. The user control unit 1100 further includes one or more input control devices 1116, which in turn cause the manipulator unit 1200 (shown in FIG. 1) to manipulate one or more took. The input control devices 1116 provide at least the same degrees of freedom as instruments 1400 with which they are associated to provide the surgeon S with telepresence, or the perception that the input control devices 1116 are integral with (or are directly connected to) the instruments 1400. In this manner, the user control unit 1100 provides the surgeon S with a strong sense of directly controlling the instruments 1400. To this end, position, force, and tactile feedback sensors (not shown) may be employed to transmit position, force, and tactile sensations from the instruments 1400 back to the surgeon's hands through the input control devices 1116.

The user control unit 1100 is shown in FIG. 1 as being in the same room as the patient so that the surgeon S can directly monitor the procedure, be physically present if necessary, and speak to an assistant directly rather than over the telephone or other communication medium. In other embodiments however, the user control unit 1100 and the surgeon S can be in a different room, a completely different building, or other remote location from the patient allowing for remote surgical procedures.

Figure 3:
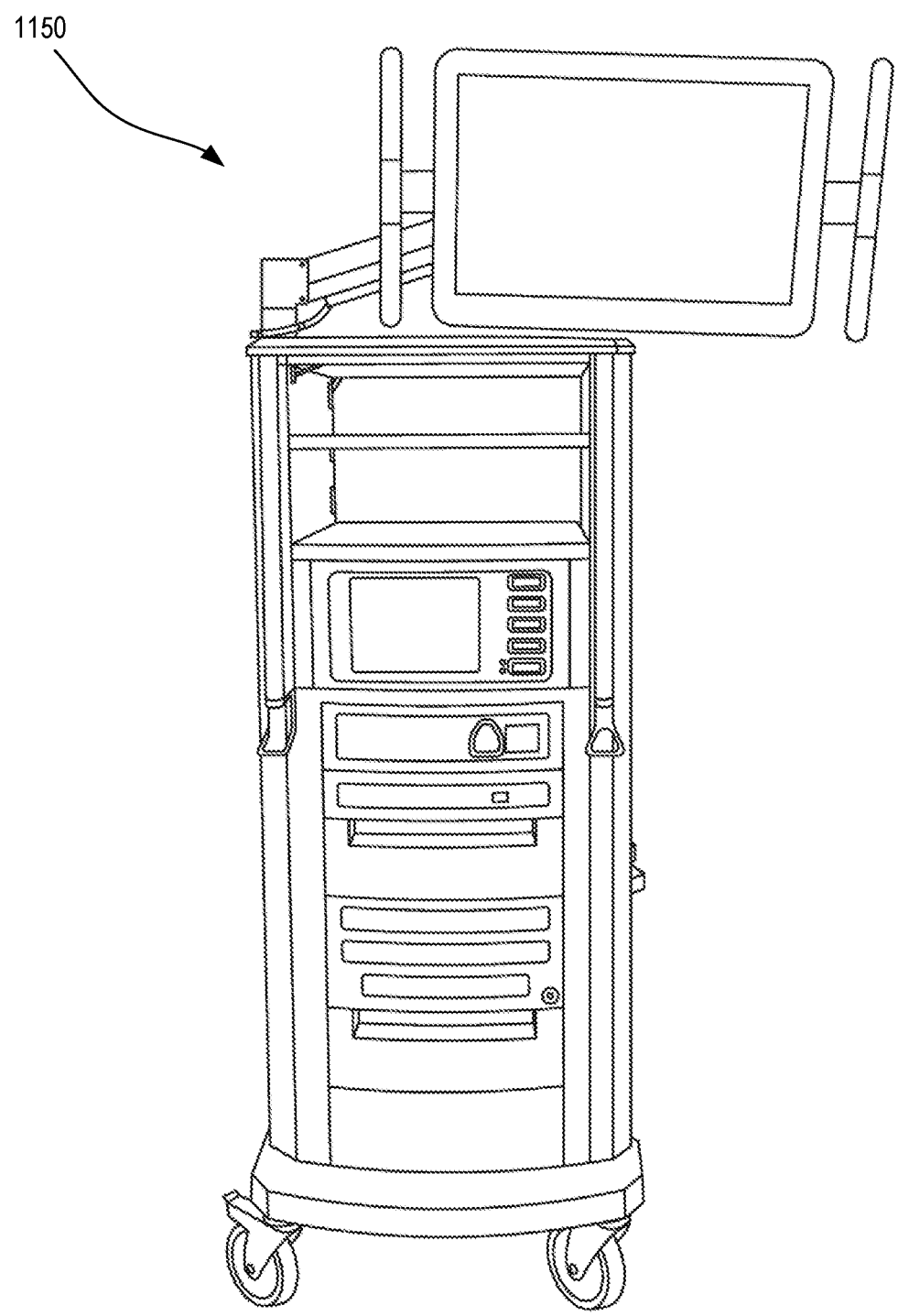
FIG. 3 is a perspective view of a user control console of the minimally invasive tele-operated surgery system shown in FIG. 1.

FIG. 3 is a perspective view of the auxiliary equipment unit 1150. The auxiliary equipment unit 1150 can be coupled with the endoscope (not shown) and can include one or more processors to process captured images for subsequent display, such as via the user control unit 1100, or on another suitable display located locally and/or remotely. For example, where a stereoscopic endoscope is used, the auxiliary equipment unit 1150 can process the captured images to present the surgeon S with coordinated stereo images of the surgical site via the left eye display 1112 and the right eye display 1114. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
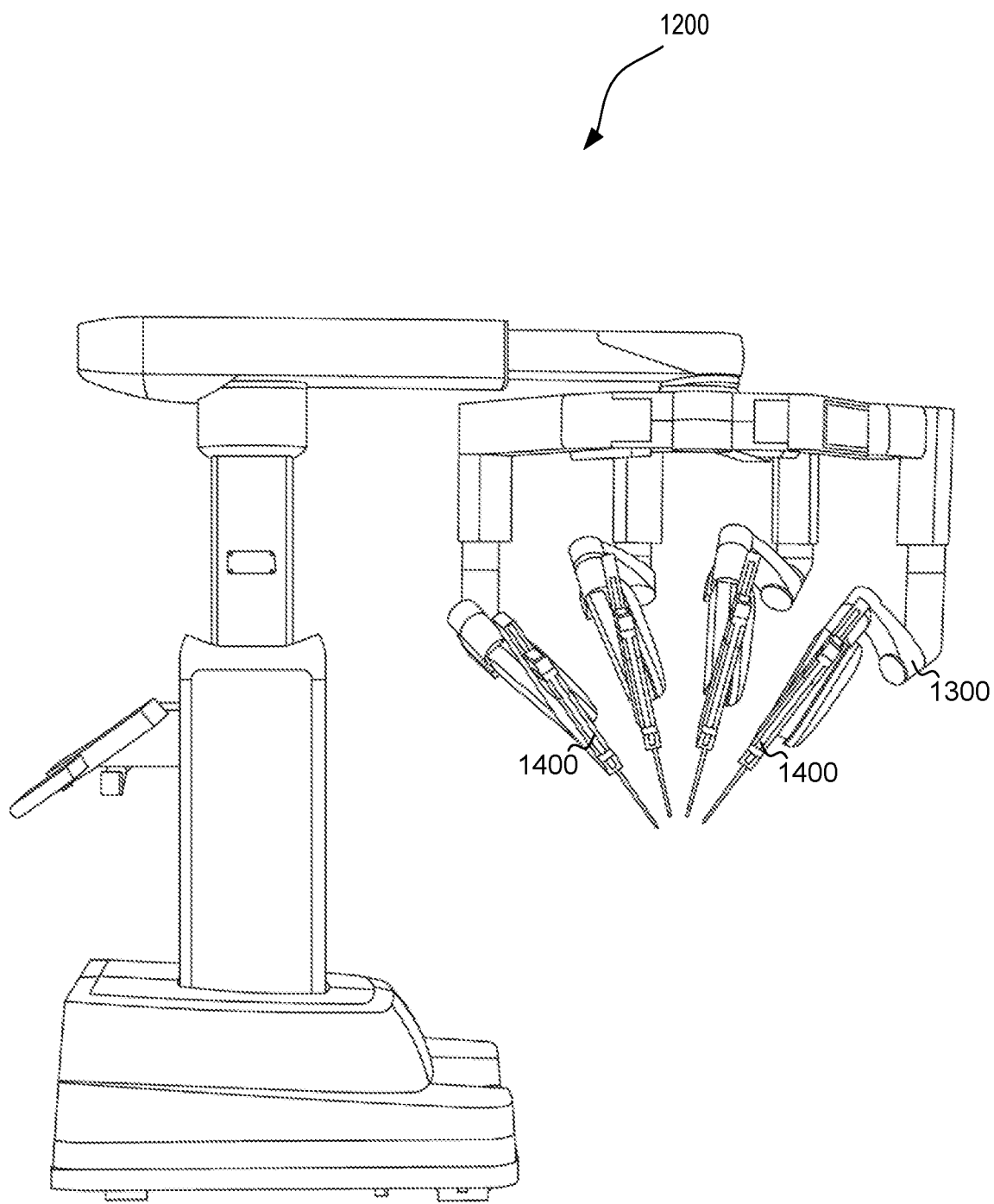
FIG. 4 is a front view of a manipulator unit, including a plurality of instruments, of the minimally invasive tele-operated surgery system shown in FIG. 1.

FIG. 4 shows a front perspective view of the manipulator unit 1200. The manipulator unit 1200 includes the components (e.g., arms, linkages, motors, sensors, and the like) to provide for the manipulation of the instruments 1400 and an imaging device (not shown), such as a stereoscopic endoscope, used for the capture of images of the site of the procedure. Specifically, the instruments 1400 and the imaging device can be manipulated by teleoperated mechanisms having a number of joints. Moreover, the instruments 1400 and the imaging device are positioned and manipulated through incisions or natural orifices in the patient P in a manner such that a kinematic remote center of motion is maintained at the incision or orifice. In this manner, the incision size can be minimized.

Figure 5C:
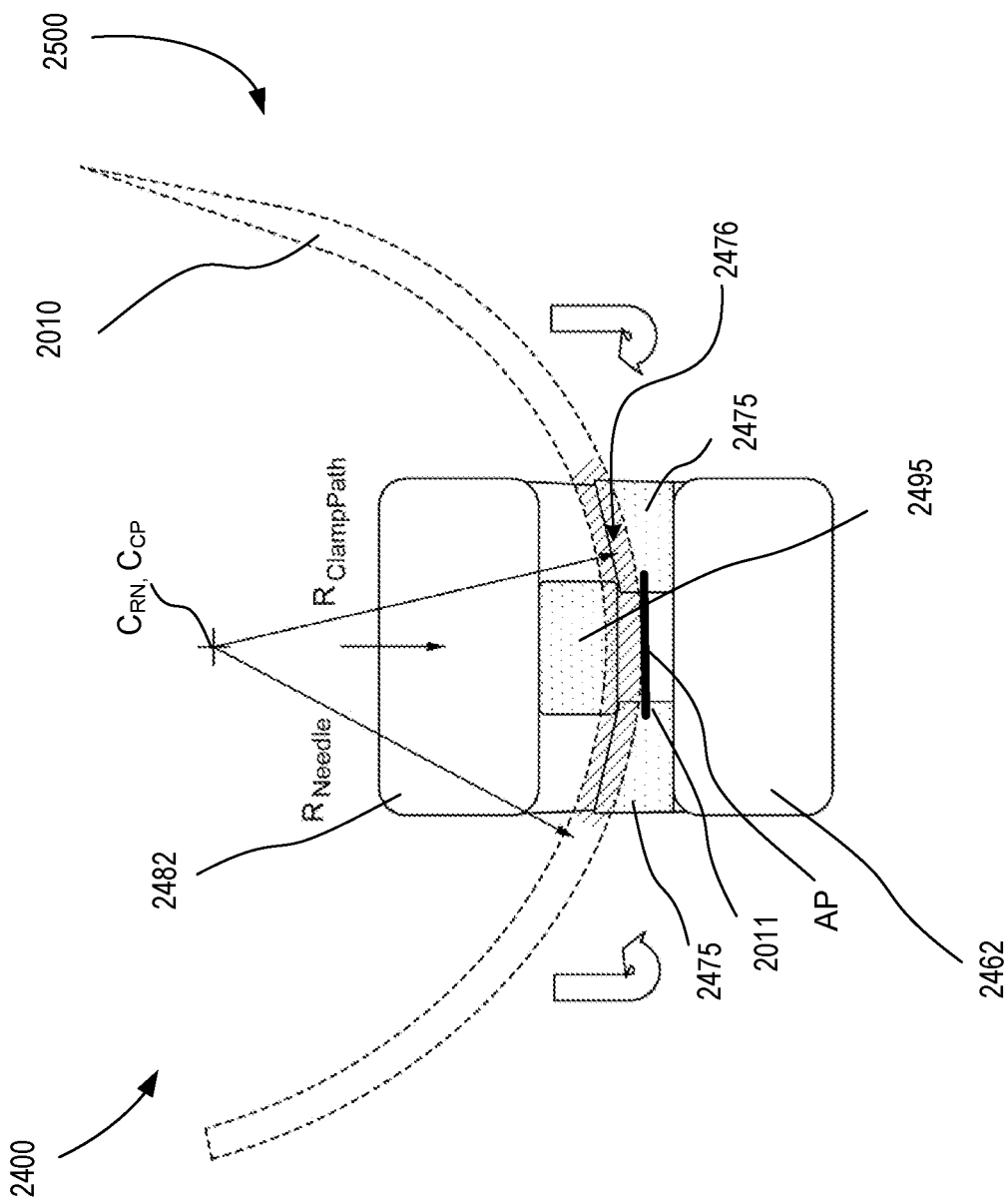
FIG. 5C is a diagrammatic cross-sectional end view of the portion of the instrument of FIG. 5B in the closed orientation viewed from line X-X shown in FIG. 5B.

FIGS. 5A-5C are diagrammatic illustrations of an instrument 2400 of a surgery system, according to an embodiment. In some embodiments, the instrument 2400 or any of the components therein are optionally parts of a surgical system that performs minimally invasive surgical procedures and which can include a manipulator unit, a series of kinematic linkages, a series of cannulas, or the like. The instrument 2400 (and any of the instruments described herein) can be used in any suitable surgical system, such as the MIRS system 1000 shown and described above. The instrument 2400 includes a clevis 2510, a first jaw 2462, and a second jaw 2482. The first jaw 2462 is coupled to the clevis 2510 and has a first gripping portion 2464 and a second gripping portion 2465. The first gripping portion 2464 on the first jaw 2462 is configured to engage a target tissue during use and, as shown in the examples of FIGS. 5A and 5B, can be located at a proximal end of the first jaw 2462. The second gripping portion 2465 can be located at an opposite distal end of the first jaw 2462 and includes a first needle alignment portion 2475 as discussed further below.

The second jaw 2482 is coupled to the clevis 2510 and has a third gripping portion 2484 and a fourth gripping portion 2485. The fourth gripping portion 2485 includes a second needle alignment portion 2495. Similar to the first gripping portion 2464 of the first jaw, the third gripping portion 2484 is also configured to engage the target tissue (not shown). Moreover, the first gripping portion 2464 and the third gripping portion 2484 are configured to cooperate with each other to more effectively engage the target tissue by clamping the tissue between opposite gripping portions on each of the jaws. As indicated by the arrow AA in FIG. 5A, the second jaw 2482 is movable with respect to the first jaw 2462 for moving between the open orientation shown in FIG. 5A, and the closed orientation shown in FIG. 5B. The second needle alignment portion 2495 of the second jaw 2482 is located opposite to, and aligned with, the first needle alignment portion 2475 when the second jaw is in the closed orientation shown in FIG. 5B.

The second jaw 2482 can be moved relative to the first jaw 2462 by any suitable mechanism. For example, in some embodiments, one or more tension members (e.g., cables, not shown) can be coupled to the second jaw 2482 to rotate the second jaw 2482 relative to the first jaw 2462 about the clevis 2510. Although the first jaw 2462 is shown as being stationary relative to the clevis 2510, in some embodiments, both the second jaw 2482 and the first jaw 2462 can move relative to the clevis 2510. In other embodiments, the second jaw 2482 can remain stationary relative to the clevis 2510 while the first jaw 2462 is moved relative to the clevis 2510.

Referring to FIG. 5A, the first needle alignment portion 2475 and the second needle alignment portion 2495 are configured to receive a curved portion 2011 of a needle 2010 between the first needle alignment portion and the second alignment portion when the second jaw 2482 is in the open orientation. The first needle alignment portion 2475 and second needle alignment portion 2495 define a clamp path 2476 (see FIGS. 5B and 5C) when the second jaw 2482 is in the closed orientation. The curved portion 2011 of the needle 2010 is received between the first and second needle alignment portions 2475, 2495 when the second jaw moves from the open orientation shown in FIG. 5A to the closed orientation shown in FIGS. 5B and 5C, during which the clamp path 2476 is formed between the first and the second jaw 2462, 2482 that closes about the curved portion 2011 of the needle. Thus, as described in greater detail along with FIG. 5C, the instrument 2400 can act as a self-righting needle holder for quickly and easily holding the needle in suturing position between the jaws.

Referring to FIG. 5C, the clamp path 2476 that is defined between the first and second needle alignment portions 2475, 2495 has a radius of curvature, $R_{ClampPath}$, that corresponds to the needle radius of curvature, $R_{Needle}$, at the curved portion 2011 of the needle. In some embodiments, the radius of curvature $R_{ClampPath}$ is equal to the needle radius of curvature $R_{Needle}$. When the needle 2010 is retained within the clamp path 2476 and while the second jaw is in the closed orientation shown in FIGS. 5B and 5C, the curved portion 2011 of the needle 2010 aligns with radius of curvature of the clamp path 2476. In this manner, a center $C_{RN}$ of the radius of curvature, $R_{Needle}$, of the needle 2010 is guided by the first and second needle alignment portions when clamping the curved portion of the needle 2010 within the clamp path 2476. In some embodiments, the clamp path radius of curvature $R_{Clamppath}$ is larger or smaller than the needle radius of curvature $R_{Needle}$ such that the instrument can hold needles of different sizes and varying curvatures in accordance with surgical requirements while still self-guiding the needle into the desired alignment and orientation in the instrument. Whether the clamp path has the same radius of curvature, $R_{ClampPath}$, or a radius that is larger or smaller than the needle radius of curvature $R_{Needle}$, the clamp path radius of curvature $R_{ClampPath}$ nonetheless includes a sufficient number of needle contact points to define the curved clamp path, engage the curved portion 2011 of the needle, and guide it into the orientation shown in FIG. 5C.

As shown by the arrows BB in FIGS. 5A-5C, when the second jaw 2482 moves to the closed orientation, it engages the needle 2010 as it clamps the needle between the jaws. During this movement to the closed orientation, the second jaw rotates the needle 2010 relative to the jaws such that the center $C_{RN}$ of the radius of curvature, $R_{Needle}$, is located at a pre-determined orientation with respect to the first and second jaws. In particular, as shown in FIG. 5C, the center $C_{RN}$ of the radius of curvature, $R_{Needle}$, is coincident with the center $C_{CP}$ of the radius of curvature $R_{ClampPath}$ of the clamp path 2476. Further, the center $C_{RN}$ of the radius of curvature, $R_{Needle}$, becomes coincident with the center $C_{CP}$ of the radius of curvature $R_{ClampPath}$ of the clamp path 2476 such that an apex, AP, of the curved needle portion 2011 matches an apex of the proximal clamp path 2476. The pre-determined orientation can be a desired orientation with respect to the instrument 2400 for performing suturing functions. For example, as shown in FIG. 5B, in some embodiments, the pre-determined orientation of the center $C_{CP}$ of the radius of curvature $R_{ClampPath}$ of the clamp path 2476 (and thus, the center $C_{RN}$ of the radius of curvature, $R_{Needle}$) intersects a longitudinal axis $A_L$ of the first jaw 2462 and the second jaw 2482 at the first and second needle alignment portions 2475, 2495 at an angle of about ninety degrees. In other embodiments, however, the radius of curvature $R_{ClampPath}$ of the clamp path 2476 intersects a longitudinal axis $A_L$ of the first jaw 2462 and the second jaw 2482 at the first and second needle alignment portions 2475, 2495 at any suitable angle.

Thus, the first and second needle alignment portions 2475 and 2495 cooperate to self-align the needle while moving the second jaw 2482 into a clamped arrangement for suturing functions. As such, when the second jaw 2482 moves from the open orientation shown in FIG. 5A to the closed orientation shown in FIGS. 5B and 5C while the curved portion 2011 of the needle is located between the first and second needle alignment portions 2475, 2495, the first and second alignment portions of the jaws are configured to engage the curved portion 2011 of the needle 2010. The jaws proceed to rotate the needle 2010 by clamping the curved portion 2011 of the needle during movement to closed orientation, such that the curved portion of the needle aligns with radius of curvature of the clamp path. In this manner, a needle 2010 can be readily clamped in place between the jaws of the instrument 2400 into a secure needle-driver, suturing arrangement with the instrument 2400. The instrument can thereby be manipulated to drive the needle 2010 while the needle is securely clamped to the instrument and retained in a desired pre-configured orientation for performing suturing functions. The aligned curvatures between the needle and the clamp path 2476 while the needle 2010 is retained in this clamped arrangement firmly retains and orients the needle with respect to the instrument.

Additionally, the inclusion of the first gripping portion 2464 and the third gripping portion 2484 provides surfaces that can engage the target tissue. In this manner, the instrument 2400 can manipulate tissue (via the first gripping portion 2464 and the third gripping portion 2484) during a first operation and then manipulate the needle 2010 (via the first and second needle alignment portions 2475, 2495) during a second operation without the need to remove the instrument from the worksite. This arrangement provides greater flexibility during surgical procedures and can minimize the operation time and reduce the number of entries and withdrawals from the surgical site. For instance, the first gripping portion 2464 and the third gripping portion 2484 can be used to perform minor adjustments in the placement and proximity of opposing tissues to be sutured, after which the first and second needle alignment portions 2475, 2495 can quickly clamp and self-orient the needle 2010 to perform suturing functions.

Although the first and second needle alignment portions 2475, 2495 are shown as being configured to rotate the needle in an upward orientation, in other embodiments, the first and second needle alignment portions 2475, 2495 (and any of the needle alignment portions described herein) can be configured to rotate the needle in a downward orientation (or any other suitable orientation). Similarly stated, the first and second needle alignment portions 2475, 2495 are shown including the center $C_{CP}$ of the radius of curvature $R_{ClampPath}$ of the clamp path 2476 on an opposite side of the second jaw 2482 as the first jaw 2462. In other embodiments, the first and second needle alignment portions 2475, 2495 can the center $C_{CP}$ of the radius of curvature $R_{ClampPath}$ of the clamp path 2476 on the same side of the second jaw 2482 as the first jaw 2462.

Although the instrument 2400 includes a first pair of gripping portions configured to engage a target tissue and a second pair of gripping portions configured to manipulate a needle, in other embodiments an instrument can include multiple sets of needle alignment portions. For example, FIGS. 6A-6D show an instrument 3400, which includes certain aspects, preferences and features as instrument 2400 described above along with FIGS. 5A-5C, except as described herein. Like numbers described herein for FIGS. 6A-6D refer to like features of FIGS. 5A-5C. Instrument 3400 shown in FIGS. 6A-6D differs from instrument by optionally including an additional needle alignment portion on each of the jaws. As discussed in greater detail below along with FIG. 6D, the additional set of needle alignment portions can provide an additional pre-determined orientation for the needle for the additional set of needle alignment portions that can be different from the pre-determined orientation shown in FIGS. 5B and 5C, such as providing a pre-determined orientation option that is 180 degrees from the other.

Referring to FIG. 6A, the instrument 3400 includes a clevis 3510, a first jaw 3462, and a second jaw 3482. The first and second jaws are each coupled to the clevis and are movable with respect to each other between an open orientation (FIG. 6A) and a closed orientation (FIGS. 6B and 6C). The first jaw 3462 includes a first proximal needle alignment portion 3471 and a first distal needle alignment portion 3475. The second jaw 3482 is coupled to the clevis 3510 and includes second proximal needle alignment portion 3491 and a second distal needle alignment portion 3495. As indicated by the pair of arrows CC in FIG. 6A, the first jaw 3462 and the second jaw 3482 are movable with respect to each other between an open orientation shown in FIG. 6A, and the closed orientation shown in FIG. 6B. The first proximal needle alignment portion 3471 of the first jaw 3462 is located opposite to, and aligned with, the second proximal needle alignment portion 3491 when the first jaw and the second jaw are in the closed orientation shown in FIG. 6B. Similarly, the first distal needle alignment portion 3475 of the first jaw 3462 is located opposite to, and aligned with, the second distal needle alignment portion 3495 when the first jaw and the second jaw are in the closed orientation shown in FIG. 6B. Although the first jaw 3462 and the second jaw 3482 are shown as moving relative to each other and to the clevis 3510, in some embodiments, only the first jaw 3462 or the second jaw 3482 can move relative to the clevis 3510 and to each other.

Referring to FIG. 6A, the first distal needle alignment portion 3475 and the second distal needle alignment portion 3495 are configured to receive a curved portion 3011 of a needle 3010 therebetween when the first jaw 3462 and the second jaw 3482 are rotated apart from each other in an open orientation. The first distal needle alignment portion 3475 and second distal needle alignment portion 3495 define a distal clamp path 3476 (see FIG. 6B) that is similar to clamp path 2476 of instrument 2400 discussed above when the first jaw 3462 and the second jaw 3482 are in the closed orientation. The curved portion 3011 of the needle 3010 can be received between the first and second distal needle alignment portions 3475, 3495 when the first and second jaws move relative to each other from the open orientation shown in FIG. 6A to the closed orientation shown in FIG. 6B in a similar manner as described for instrument 2400. Thus, the instrument 3400 can likewise act as a self-righting needle holder for quickly and easily holding the needle in a suturing position at a distal end of the instrument between the jaws, which operates similar to the self-righting needle functions described above for instrument 2400.

In addition, the first proximal needle alignment portion 3471 and second proximal needle alignment portion 3491 of instrument 3400 further define a proximal clamp path 3477 (see FIGS. 6C and 6D) in addition the distal clamp path 3476. In some embodiments, the proximal clamp path 3477 can function in a similar manner as the distal clamp path 3476 to provide similar self-righting and needle clamping functionality to that provided by distal clamp path 3476, but can also do so at a second, proximal position along the instrument in comparison with the distal clamp path 3476. In some circumstances, it can be beneficial to have more than one self-righting needle position along the instrument that can provide another option for performing suturing functions with respect to the particular surgical environment, such as geometric access factors available to the suture site, the freedom of movement available for moving within the access space for suturing functions, or the clamp force and needle driving requirements for forming sutures in the particular tissue and location for the surgical environment. In other embodiments, the proximal clamp path 3477 can be configured to function in a different manner compared with distal clamp path 3476, such as to provide a different self-righting needle holding functionality that can, for example, provide a different needle holding orientation, be configured to clamp different types or sizes of needles, or provide differing self-righting or clamping retention abilities.

Referring to FIGS. 6A and 6B, the first and second proximal needle portions 3471 and 3491 can be configured to provide different needle holding functionality compared with the distal needle portions 3475 and 3495. Similar to the first and second distal needle portions 3475 and 3495, the first and second proximal needle portions 3471 and 3491 can hold the curved portion 3011 of the needle 3010 between the opposing needle portions when the needle is received between them and the first and second jaws move relative to each other, such as from the open orientation shown in FIG. 6A to the closed orientation shown in FIGS. 6B and 6C. In a similar manner, the proximal clamp path 3477 can also be formed between the first and the second jaws 3462, 3482 when in the closed orientation, such that the proximal clamp path 3477 also closes about the curved portion 3011 of the needle. However, different from the distal clamp path 3476 the proximal clamp path 3477 in the embodiment shown in FIG. 6C is configured to provide a proximal needle orientation between the first and second proximal needle alignment portions 3471 and 3491 that differs from the distal needle orientation between the first and second distal needle alignment portions 3475 and 3495. In particular, the embodiment of FIG. 6C includes a proximal needle orientation that is about 180 degrees opposite from the distal needle orientation. Stated differently, the embodiment shown in FIGS. 6C and 6D includes a distal needle orientation that is directed toward the second jaw 3482 with respect to the first jaw 3462 (e.g., directed in an upward orientation if the second jaw is oriented upward with respect to the first jaw), and an opposite proximal needle orientation that is directed toward the first jaw 3462 with respect to the second jaw 3482 (e.g., directed in a downward orientation if the first jaw is oriented downward with respect to the second jaw).

Thus, in a similar manner as instrument 2400 discussed above along with FIGS. 5A-5C, the instrument 3400 can likewise act as a self-righting needle holder for quickly and easily holding the needle in a suturing position at a distal end of the instrument between the jaws. In addition, the instrument 3400 can further provide additional self-righting needle holding functionality at a proximal position along the instrument in comparison with the distal needle alignment portions 3475 and 3495. Moreover, instrument 3400 is configured in the embodiment shown in FIGS. 6C and 6D to hold the needle in a self-righting proximal orientation that is opposite from the orientation of the self-right distal orientation. Stated differently, the embodiment of instrument 3400 can hold the needle 3010 in two opposite orientations to provide options as appropriate for the surgical environment, while still be providing self-righting functionality for both of the opposite orientations.

Providing the opposite needle holding orientations along with self-righting functionality for each of these orientations when clamping the needle (see FIGS. 6A and 6B) can be beneficial for various surgical environments and conditions, as well as for user preferences. For example, many sutures disposed at various locations on a patient can be easier to perform by driving the needle 3010 into the target tissue from a particular location based on surgical factors and conditions, such as many wound locations encouraging needle access to occur from below the wound (e.g., for suturing a wound located on the underside of a body part that should not be moved, or suturing from within a body cavity). The distal needle orientation shown in FIG. 6B, as an example, can provide an advantageous orientation for guiding the needle from an underside for these environments. Further, other surgical environments can encourage driving the needle into the target tissue (not shown) from a different orientation and direction of movement, such as driving the needle into the tissue in a clockwise or counter-clockwise direction from a position disposed above the wound based on surgical factors like wound geometry or tissue tension.

The proximal needle orientation shown in FIG. 6C, as an example, can be an advantageous orientation for guiding the needle for these sutures. Providing the proximal and distal needle orientation with opposite orientations in the same instrument 3400 along with configuring the instrument to provide self-righting functionality for the needle with either left or right handed orientations, can enable the user to quickly change the orientation of the needle that is held in the instrument, and to do so without withdrawing/re-engaging the instrument 3400 from the surgical area (i.e., for easily changing between the orientation of FIG. 6B vs. 6C). The embodiment of instrument 3400 can be configured to receive the needle between the jaws when in the open orientation with the needle tip placed on either lateral side of the instrument based on left or right-handed preferences and/or surgical factors while still providing self-righting functionality to guide the needle into the corresponding orientation at which it is held for driving the needle. Thus, instrument 3400 can provide significant flexibility for adapting the orientation of the needle 3010 during use as appropriate according to the surgical environment, user preferences, ease of access for suturing, etc. The instrument 3400 can further do so without incurring time-consuming instrument adjustments, while avoiding increased risk of contamination from the removal/entry of the instrument, and while firmly clamping the needle in the appropriate orientation when the jaws clamp on the needle and are located in the closed orientation.

The self-righting actions shown in FIG. 6B can operate in a similar manner as was discussed above along with instrument 2400 along with moving the first and second jaws 3462 and 3482 with respect to each other into the closed, clamped orientation. Similarly, the self-righting actions shown in FIG. 6C can operate in a similar, but opposite manner to provide an opposite orientation for the needle. With reference to FIG. 6D along with FIG. 6C, when instrument 3400 receives the needle 3010 between the first proximal needle orientation portion 3471 and the corresponding and opposed second proximal needle orientation portion 3491, and the first and second jaws move with respect to each other into the closed orientation shown in FIG. 6D, the needle 3010 is clamped between the first and second needle orientation portions. When in the closed orientation of FIG. 6D, the proximal clamp path 3477 is defined between the first and the second proximal needle alignment portions 3471, 3491, which has a radius of curvature, $R_{ClampPath}$, that corresponds to the needle radius of curvature, $R_{Needle}$ at the curved portion 3011 of the needle. The proximal clamp path 3477 includes a sufficient number of needle contact points to define the curved clamp path, engage the curved portion 3011 of the needle, and guide it into the opposite proximal orientation shown in FIGS. 6C and 6D vs. the distal orientation shown in FIG. 6B.

As shown by the arrows EE in FIGS. 6C and 6D, when the second jaw 3482 moves to the closed orientation and clamps the needle between the jaws, it rotates the needle 3010 relative to the jaws such that the center $C_{RN}$ of the radius of curvature, $R_{Needle}$, is located at a pre-determined distal orientation with respect to the first and second jaws. In particular, as shown in FIG. 6C, the center $C_{RN}$ of the radius of curvature, $R_{Needle}$, becomes coincident with the center $C_{CP}$ of the radius of curvature $R_{ClampPath}$ of the clamp path 3476 such that an apex, AP, of the curved needle portion 3011 matches an apex of the proximal clamp path 3477. The pre-determined orientation can be a desired orientation with respect to the instrument 3400 for performing suturing functions. For example, as shown in FIG. 5B, in some embodiments, the pre-determined orientation of the center $C_{CP}$ of the radius of curvature $R_{ClampPath}$ of the clamp path 3477 (and thus, the center $C_{RN}$ of the radius of curvature, $R_{Needle}$) can intersect a longitudinal axis $A_L$ of the first jaw 3462 and the second jaw 3482 at the first and second proximal needle alignment portions 3471, 3491 at an angle of about ninety degrees. In other embodiments, however, the radius of curvature $R_{ClampPath}$ of the clamp path 3477 can intersect a longitudinal axis $A_L$ of the first jaw 3462 and the second jaw 3482 at the first and second needle alignment portions 3471, 3491 at any suitable angle.

Thus, the first and second proximal needle alignment portions 3471 and 3491 can cooperate to self-align the needle in either of the pair of opposite orientations shown in the FIG. 6B vs. 6C options, as well as to allow the needle to easily be switched between the orientations. As such, when the first and second jaws 3462 and 3482 move with respect to each other from the open orientation shown in FIG. 6A to the closed orientations shown in FIGS. 6B-6D, and while the curved portion 3011 of the needle is located between the corresponding needle alignment portions (3471 and 3491, or 3475 and 3495), the needle alignment portions of the jaws are configured to engage the curved portion 3011 of the needle and rotate the needle 3010 into the driving orientation at which it is held for suturing functions.

Figures 7A, 7B:
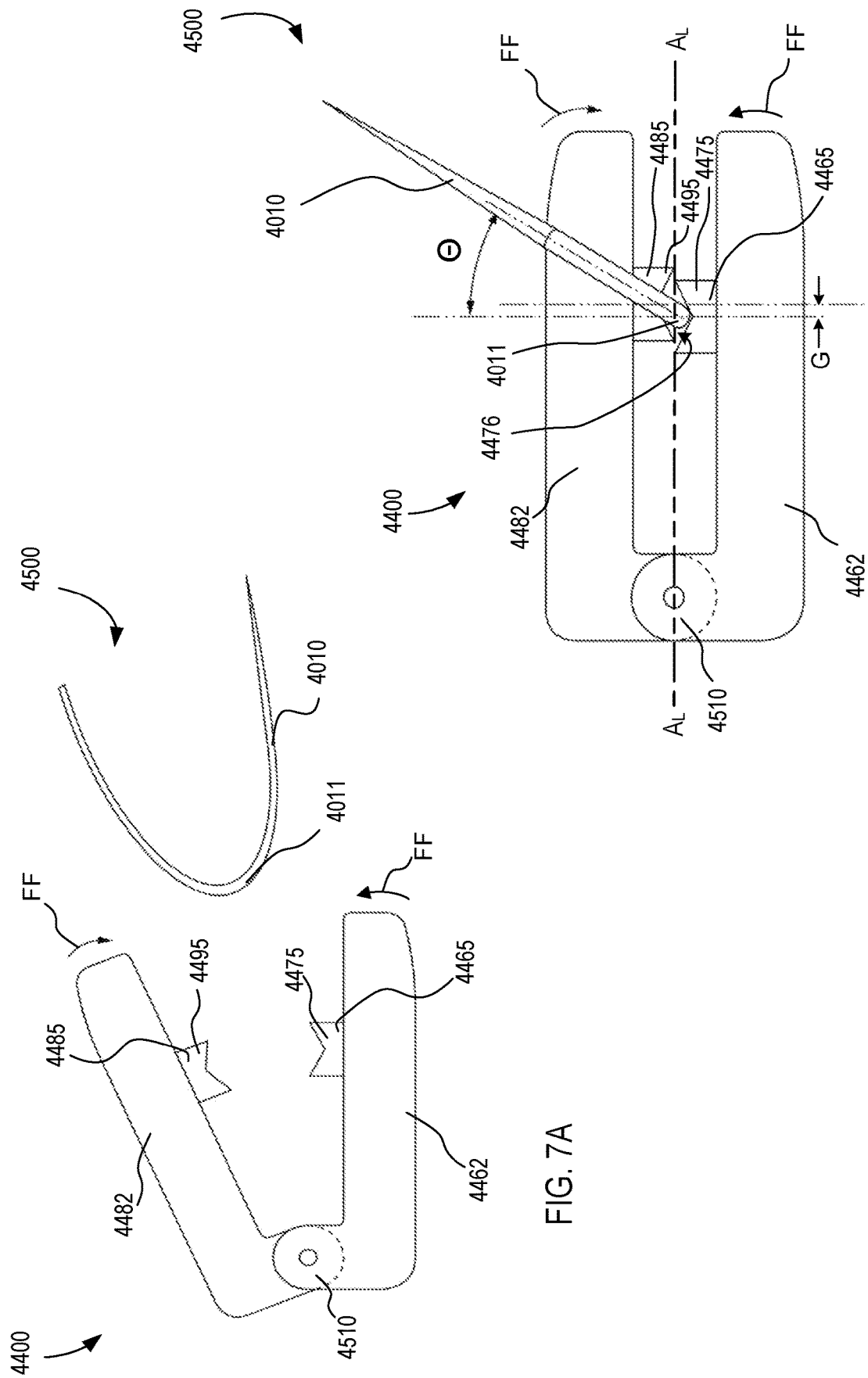
FIG. 7A is a diagrammatic side view of a portion of an instrument of a surgery system shown in an open orientation, according to an embodiment.
FIG. 7B is a diagrammatic side view of the portion of the instrument of FIG. 7A shown in a closed orientation.

The corresponding pairs of needle alignment portions in FIGS. 6A-6D are shown as being configured to rotate the needle into one of the orientations shown in FIGS. 6B and 6C such that the needle can be oriented perpendicular with respect the longitudinal axis $A_L$. In other embodiments, the needle alignment portions (and any of the needle alignment portions described herein) can be configured to rotate the needle in various different orientations and combinations of orientations. For example, FIGS. 7A and 7B show an instrument 4400, which can provide different needle alignment orientations from those discussed above. The instrument includes certain aspects, preferences and features as are described above along with instruments 2400 and 3400, except as described herein. Like numbers described herein for FIGS. 7A and 7B refer to like features of FIGS. 5A-5C and 6A-6D. Instrument 4400 shown in FIGS. 7A and 7B differs from the distal needle orientation portions of instruments 2400 and 3400 by optionally being configured to guide the needle 4010 during self-righting movements to be oriented in a pre-determined needle holding orientation for the clamped needle 4010 that is shown in FIG. 7B, which can be configured to have an orientation that is not perpendicular with respect to the longitudinal axis $A_L$ of the instrument 4400. Stated differently, the clamped needle 4010 is held in a non-normal orientation with respect to the longitudinal axis of the instrument 4400 such that the needle defines an offset angle of rotation, Θ, vs the perpendicular positions of the previous instruments 2400 and 3400.

The embodiment of FIGS. 7A and 7B can be configured in a similar manner as instruments 2400 and 3400. Thus, instrument 4400 can include one or more tissue contact portions (e.g., gripping portions; not shown in FIGS. 7A and 7B), as well as one or more additional sets of needle orientation portions (also not shown in FIGS. 7A and 7B) that can hold the needle in multiple different and/or similar orientations within the instrument 4400 during needle driving functions. Further, as is shown in FIGS. 7A and 7B, the instrument 4400 can also include a corresponding set of needle orientation portions 4465 and 4485 that are configured to provide the offset angle of rotation arrangement shown in FIG. 7B for needle driving functions, and can do so without including the additional portions shown and discussed above along with instruments 2400 and 3400. Rather, this arrangement can be configured to provide customized orientations for holding the needle for suturing function that can provide benefits for particular surgical situations and types of surgical functions. As an example, in a situation in which access to a wound to be sutured is limited to an elongate distal region, such as within a patient's throat or other similarly shaped cavity, customized holding orientations for the needle within the instrument 4400 can be beneficial for the needle driving functions, which when combined with some of the beneficial aspects and features discussed above pertaining to self-righting functionality and options for easily changing or adjusting the needle without removing the instrument 4400 from the surgical environment, can provide a customized instrument that is well adapted for the particular surgical functions along with providing additional benefits pertaining to quickly and easily adjusting the instrument in vivo.

Referring to FIGS. 7A and 7B, the instrument 4400 includes a clevis 4510, a first jaw 4462, and a second jaw 4482. The first jaw 4462 is coupled to the clevis 4510 and has a first gripping portion 4465. The second jaw 4482 is coupled to the clevis 4510 and the first jaw 4462, and has a second gripping portion 4485. The first gripping portion 4465 on the first jaw includes a first needle alignment portion 4475. Likewise, the second gripping portion 4485 on the second jaw includes a second needle alignment portion 4495. As indicated by the arrow EE in FIGS. 7A and 7B, the second jaw 4482 is movable with respect to the first jaw 4462 for moving between the open orientation shown in FIG. 7A, and the closed orientation shown in FIG. 7B. The second needle alignment portion 4495 of the second jaw 4482 is located opposite the first needle alignment portion 4475 when the first and second jaws are in the closed orientation shown in FIG. 7B. However, unlike instruments 2400 and 3400, the first needle alignment portion 4475 is not aligned with the second needle alignment portion 4495 when the first and second jaws are in the closed orientation.

Rather, as shown in FIG. 7B, the first needle alignment portion 4475 on the first jaw and the second needle alignment portion 4495 on the second jaw are offset by a particular distance as appropriate for the intended suturing usage of the instrument 4400, which in some embodiments can be a customized longitudinal offset distance, G. In some embodiments, the offset distance G can include the second needle configuration portion 4495 of the second jaw 4482 being distally offset with respect to the first needle configuration portion 4475 along the longitudinal axis, $A_L$, of the instrument 4400 as is shown in FIG. 7B. In other embodiments, the offset distance G can have an offset arrangement such that the first needle configuration portion 4475 is distally offset along the longitudinal axis $A_L$ with respect to the second needle configuration portion 4495. In other embodiments, the offset distance and customized arrangement of the first and second needle configuration portions can be different in various ways that provide various non-normal holding orientations for the needle, such as providing needle orientations in opposite directions (e.g., downward to the extent needle 4010 shown in FIG. 7B can be considered an upward orientation), or in other arrangements such as configuring the needle to be primarily proximally oriented when the needle is held in a needle driving orientation.

Referring to FIG. 7B, the distal offset distance G between the corresponding needle configuration portions allows instrument 4400 to maintain self-righting needle functionality in a similar manner as discussed above along with instruments 2400 and 3400 while also clamping the curved portion of the needle therebetween. However, the distal offset distance G results in providing a non-normal orientation when forming the clamp path 4476. In other words, the offset distance between the needle configuration portions 4475 and 4495 can define a clamp path 4476 that is distally angled such that the clamp path lies within a lateral plane with respect to the longitudinal axis, $A_L$, which is non-normal and defines an angle, θ, extending away from the longitudinal axis. Thus, as shown in FIG. 7B, when the instrument 4400 guides the needle 4010 to provide self-righting functionality similar to the functionality discussed above along with instruments 2400 and 3400, the clamped orientation in which the needle 4010 is held for needle driving functions is a non-normal orientation. However, the needle orientation is likewise coincident with the clamp path 4476, such that the orientation of the needle when held in the needle driving orientation also defines an angle, Θ, in which the needle is rotated from a perpendicular orientation shown in FIGS. 5A-5C and 6A-6D. Stated differently, the needle confirmation portions 4475 and 4495 can be offset with respect to each other in order to provide customized orientations for the needle during needle driving functions.

In some embodiments, an instrument can combine self-righting needle holder functionality with tissue engaging functionality in an instrument having multiple degrees of freedom for moving in many directions, such as providing self-righting needle driving functionality in a wrist mechanism without limiting its range of motions. For example, FIGS. 8-11C show various views of an instrument 5400, according to an embodiment, which generally includes the same preferences and features as described above along with instruments 2400 and 3400 except as described hereafter in an instrument configured to move in multiple directions. Accordingly, like numbers refer to like features as described above. In some embodiments, the instrument 5400 or any of the components therein are optionally parts of a surgical assembly that performs minimally invasive surgical procedures, and which can include a manipulator unit, a series of kinematic linkages, a series of cannulas, or the like. The instrument 5400 (and any of the instruments described herein) can be used in any suitable surgical system, such as the MIRS system 1000 shown and described above. The instrument 5400 includes a transmission assembly 5700 (that can function as an actuator mechanism), an instrument shaft 5410, a wrist assembly 5500, and an end effector 5460.

The wrist assembly 5500 includes a link configured as a proximal first link (not shown), a distal second link 5610, and a first jaw 5462 and a second jaw 5482 that are both part of the end effector 5460. Each of the pair of jaws are coupled to the distal second link 5610 in an opposing relationship with each other, so that the pair of jaws can cooperate with each other to clamp, grasp, or otherwise interface with a target tissue (not shown). The instrument 5400 further includes one or more tension members (not shown), which have been omitted in FIGS. 8-11C to more clearly show features pertaining to the needle holding features. However, the instrument 5400 generally includes multiple tension members (not shown) that couple the transmission mechanism 5700 to the wrist assembly 5500. The instrument 5400 is configured such that movement of the tension members can produce rotation of the wrist assembly 5500 (i.e., pitch rotation) about a first axis of rotation, $A_1$, yaw rotation of the end effector 5460 about a second axis of rotation, $A_2$, grip rotation of the jaws of the end effector 5460 about the yaw axis, or any combination of these movements. Thus, the instrument 5400 is configured to perform a variety of articulation movements along portions of the wrist assembly 5500 and the end effector 5460.

The transmission mechanism 5700 produces movement of the plurality of tension members (not shown), which operate to produce the desired articulation movements (pitch, yaw, or grip) at the wrist assembly 5500. Specifically, the transmission mechanism 5700 includes components and controls to move some of the tension members in a proximal direction (i.e., to pull in certain tension members) while simultaneously allowing the distal movement (i.e., releasing or "paying out") of other of the tension members in equal lengths. In this manner, the transmission mechanism 5700 can maintain the desired tension within the tension members, and can ensure that the lengths of the tension members are conserved (i.e., moved in equal amounts) during the entire range of motion of the wrist assembly 5500. In some embodiments, for example, the transmission assembly 5700 can be any of the transmission assemblies shown and described in International Patent Application No. PCT/US2017/062258, (filed Nov. 14, 2017), entitled "Cable Length Conserving Medical Instrument," which is incorporated herein by reference in its entirety. In other embodiments however, conservation of the lengths of the tension members is not required.

Figure 8:
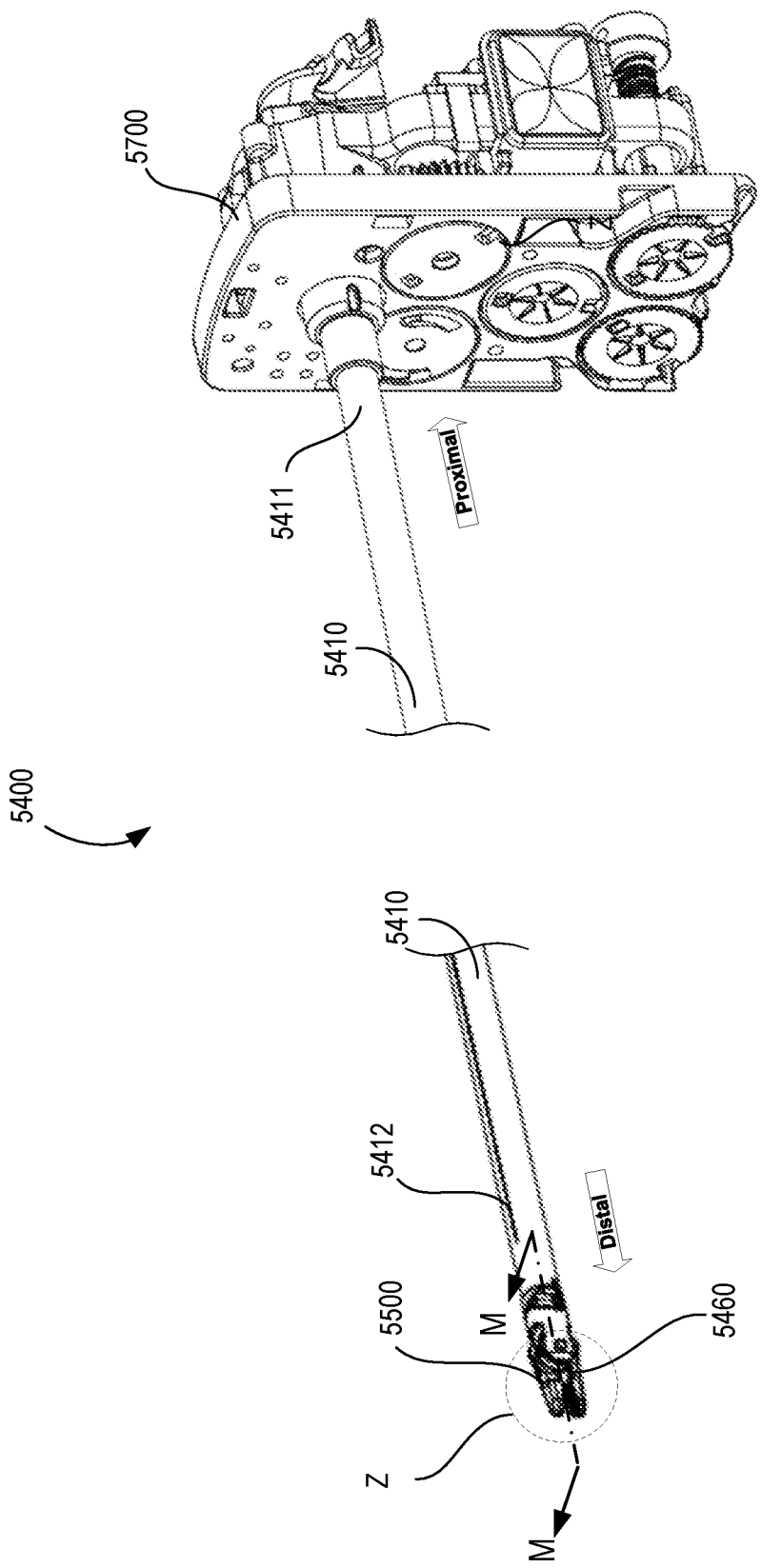
FIG. 8 is a perspective view of an instrument of a surgery system in a first orientation, according to an embodiment.

Referring now to FIG. 8, the articulable wrist mechanism 5500 of the instrument 5400 is coupled to the shaft 5410, which can be any suitable elongated shaft that couples the wrist assembly 5500 to the transmission mechanism 5700. Specifically, the instrument shaft 5410 includes a proximal end portion 5411 that is coupled to a housing of the transmission mechanism 5700, and a distal end portion 5412 that is coupled to the wrist assembly 5500. The instrument shaft 5410 defines a passageway or series of passageways through which the tension members (not shown) and other components (e.g., electrical wires, ground wires, or the like) can be routed from the transmission mechanism 5700 to the wrist assembly 5500. Although shown as being cylindrical, in other embodiments the instrument shaft 5410 can have any suitable shape.

Figure 9A:
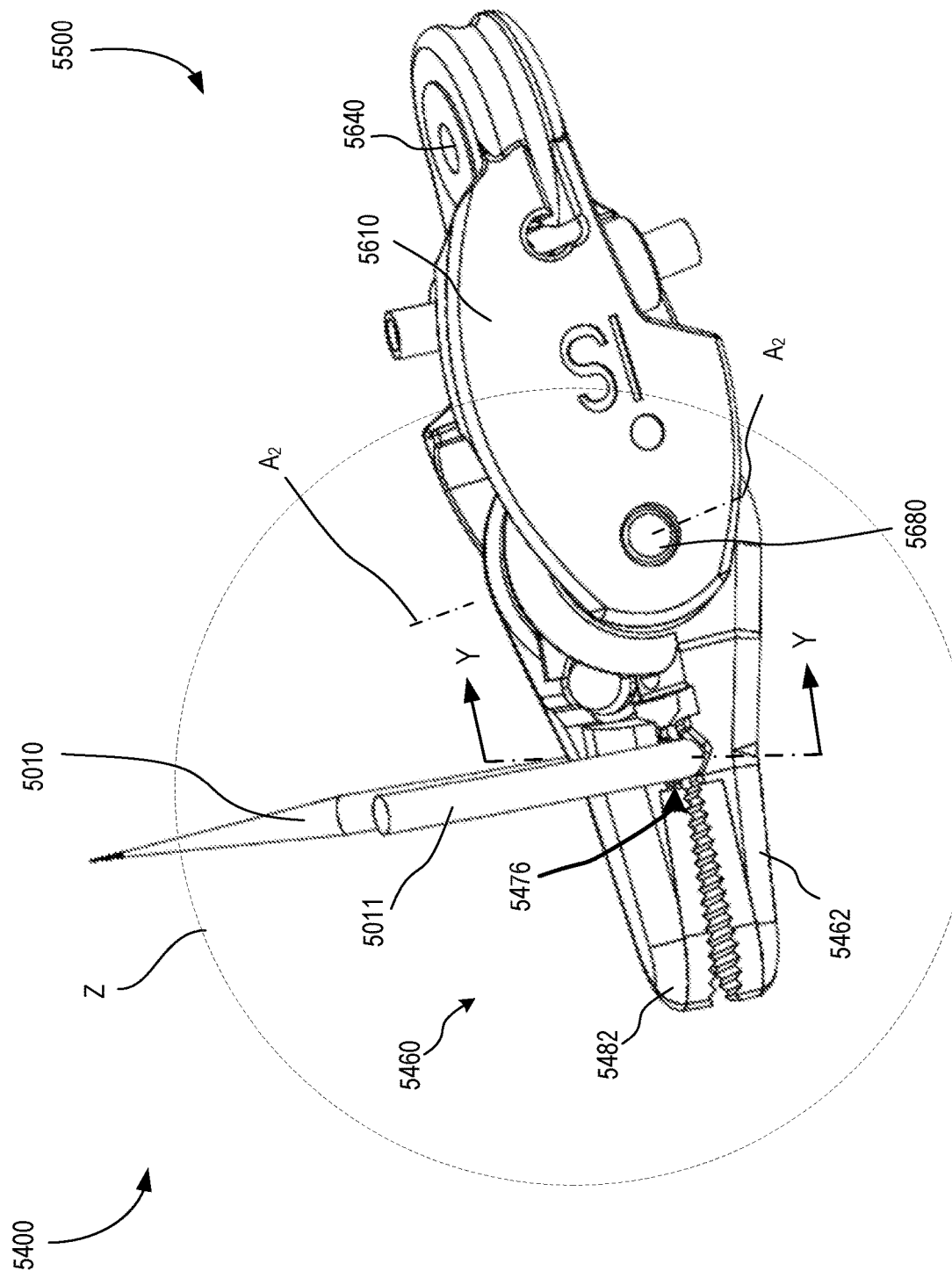
FIG. 9A is an enlarged, side perspective view of a distal end portion of the instrument indicated by the region Z shown in FIG. 8, according to an embodiment, in a first, closed orientation clamping a needle between the instrument jaws, in which the first link and smaller components, such as the idler pulleys and tension members, have been removed for clarity.
Figure 9B:
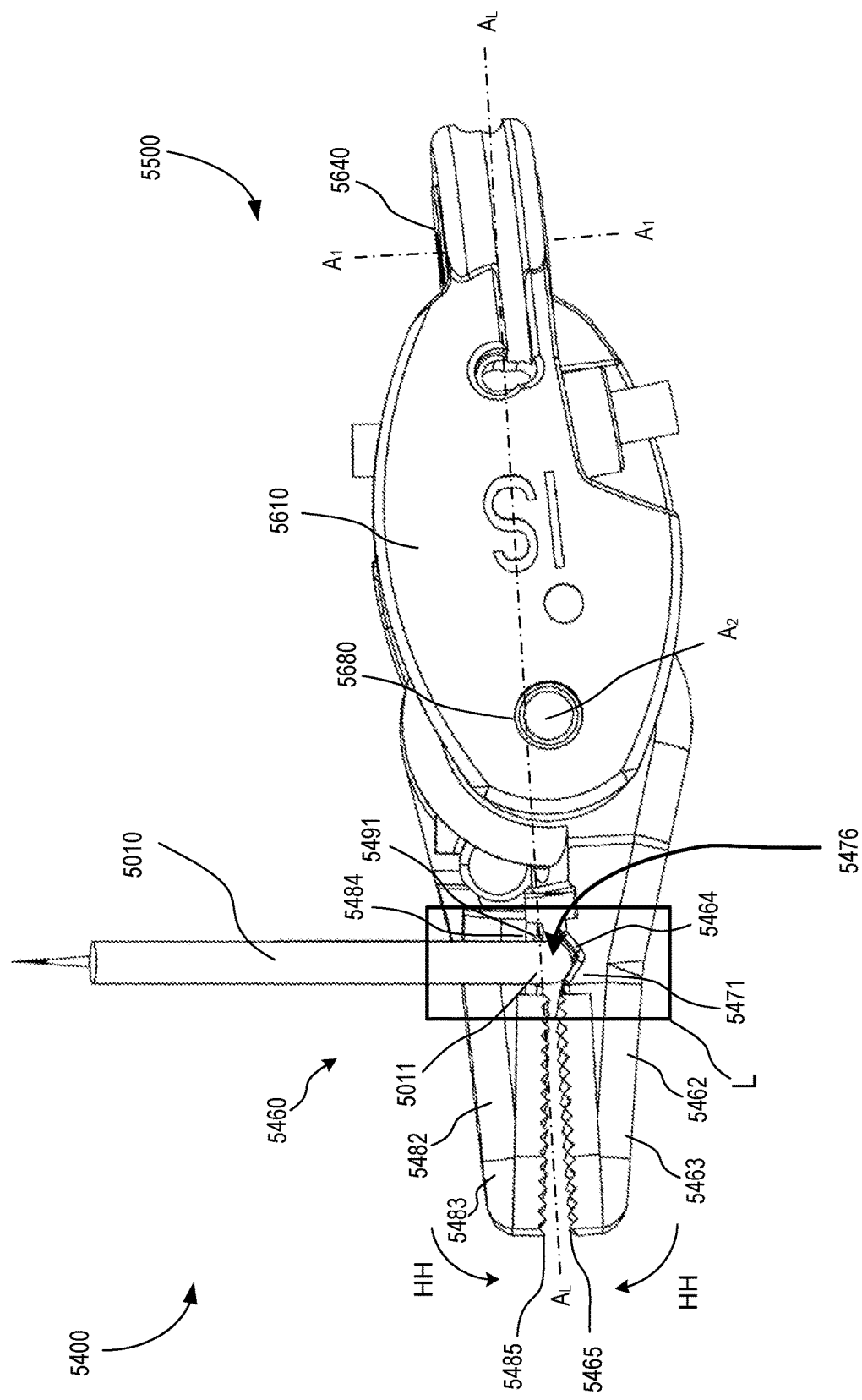
FIG. 9B is a side view of the distal end portion of the instrument shown in FIG. 9A.
Figure 9C:
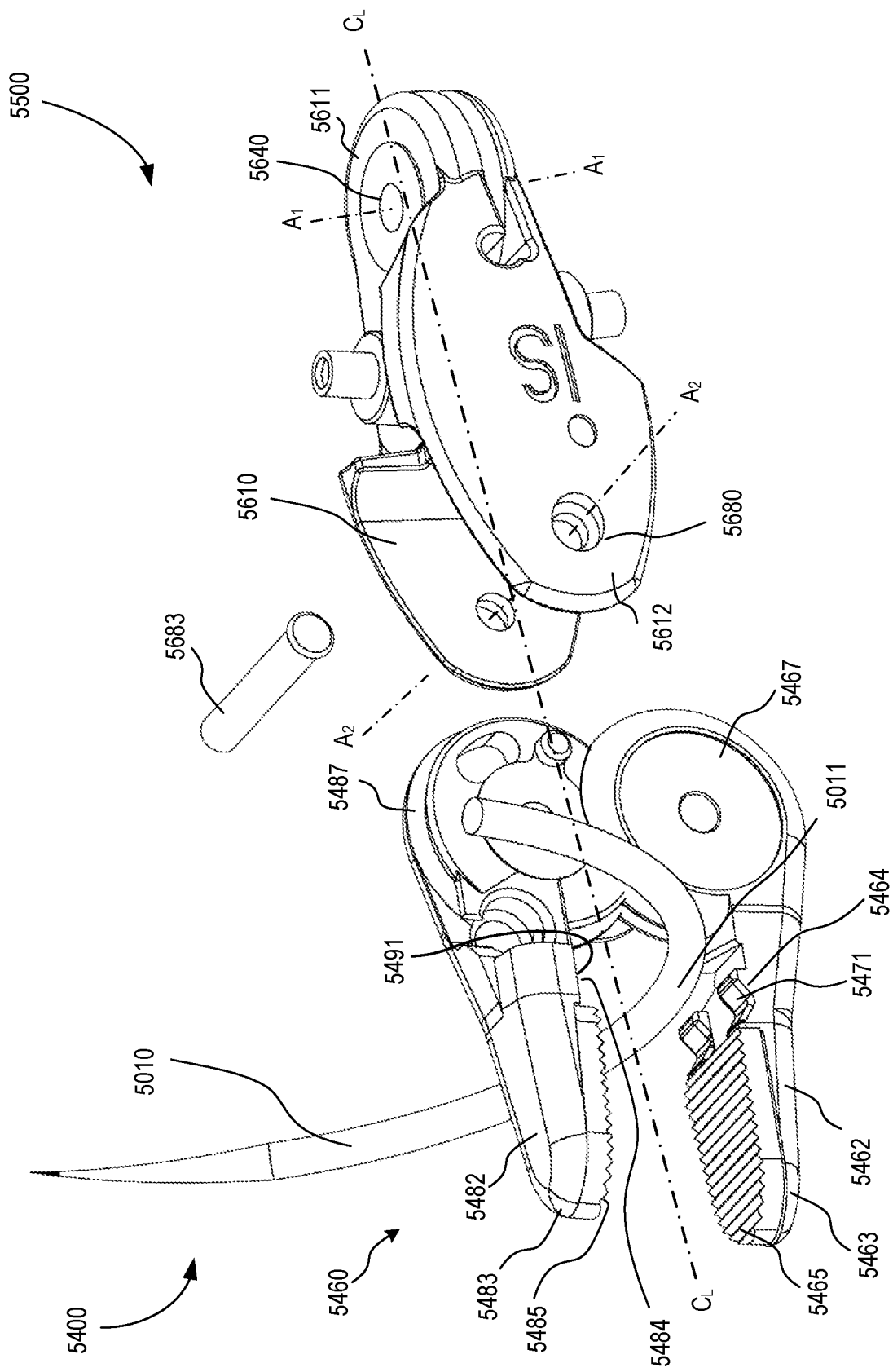
FIG. 9C is an exploded, perspective view of the distal end portion of the instrument of FIG. 9A.

Referring now to FIGS. 9A-9C, the wrist assembly 5500 includes a proximal first link (not shown) that is coupled to the distal end portion 5412 of the instrument shaft 5410, and a distal second link 5610, which is articulably coupled to an end effector 5460. In this manner, the first link (not shown) and the second link 5610 form the wrist assembly 5500 having a first axis of rotation $A_1$ (also referred to as the pitch axis) about which the second link 5610 can rotate relative to the first link (not shown). As shown in FIG. 9C, the first link (not shown) and the second link 5610 define a longitudinal centerline $C_L$ that intersects the pitch axis $A_1$ when the instrument is in an initial (or "straight") configuration). The first link (not shown) defines various bores and/or guide paths that can contain (or allow passage of) various components of the wrist assembly including the tension members (not shown) and various electrical components and connections.

The distal second link 5610 has a proximal end portion 5611 and a distal end portion 5612. The proximal end portion 5611 includes a joint portion 5640 that is rotatably coupled to the joint portion of the first link (not shown). The distal end portion 5612 of the second link 5610 includes a connector 5680 that is coupled to the end effector 5460. In this manner, the first jaw 5462 and the second jaw 5482 of the end effector 5460 can rotate relative to the second link 5610 about a second axis of rotation $A_2$ (also referred to as the yaw axis). The connector 5680 is a pin-type connector and includes the pin 5683 which is supported by (and placed within) the pin openings 5682. In some embodiments, the connector 5680 can include any of the structure and features of the pinned joints shown and described in U.S. Pat. No. 9,204,923 B2 (filed Jul. 16, 2008), entitled "Medical Instrument Electronically Energized Using Drive Cables," which is incorporated herein by reference in its entirety. As shown in FIGS. 9B and 9C, the second axis of rotation $A_2$ (also referred to as the yaw axis) is non-parallel to the pitch axis $A_1$. Thus, the instrument 5400 provides for up to three degrees of freedom (i.e., a pitch motion about the first axis of rotation $A_1$, a yaw rotation about a second axis of rotation $A_2$, and a grip motion about the second axis of rotation $A_2$.

Referring now to FIGS. 9C, 10A and 10B, the first jaw 5462 of the end effector 5460 includes a proximal pulley portion 5467 and a distal end portion 5463. Similarly, the second jaw 5482 includes a proximal pulley portion 5487 and a distal end portion 5483. The proximal pulley portions 5467, 5487 of the jaws 5462, 5482 are each rotatably coupled to the distal end portion 5612 of the distal second clevis 5610 at connector 5680 via pin 5683 to rotate about the second axis $A_2$. One or more of the tension members (not shown) are coupled to each of the proximal pulley portions 5467, 5487 to drive movement of a corresponding one of the jaws 5462, 5482 including moving the jaws with respect to each other and rotating the jaws with respect to the second link 5610, such as when a tension member (not shown) applies a tensile force along a perimeter portion of a proximal pulley portion 5467, 5487. In this manner, the first and second jaws 5462, 5482 can each rotate about the pin 5683 and relative to the second link 5610 via the second axis of rotation $A_2$. As such, application of a force by the corresponding tension members (not shown) to each of the proximal pulley portions 5467, 5487 can produce a torque on the first jaw 5462 and the second jaw 5482 about a yaw axis, which can result in rotation of the first jaw 5462 and the second jaw 5482, or the application of a gripping force between the jaws.

The first jaw 5462 includes a first distal gripping portion 5465 located at a distal end portion thereof, which further includes a first proximal gripping portion 5464 and a first distal gripping portion 5465. The second jaw 5484 likewise includes a second contact portion 5483 located at a distal end thereof, which further includes a second proximal gripping portion 5484 and a second distal gripping portion 5485. The first distal gripping portion 5465 on the first jaw 5462 and the second distal gripping portion 5485 on the second jaw 5482 are each configured to engage a target tissue during use and, as shown in the examples of FIGS. 9A-9C, can be located at a distal end of the corresponding first and second jaw 5462, 5482. The first proximal gripping portion 5464 can be located at an opposite proximal end of the first jaw 5462, and the second proximal gripping portion 5484 can be located at an opposite proximal end of the second jaw 5482. In addition, as discussed further below, the first proximal gripping portion 5464 includes a first needle alignment portion 5471, and the second proximal gripping portion 5484 includes a second needle alignment portion 5491.

The first distal gripping portion 5465 and the second distal gripping portion 5485 are configured to cooperate with each other to more effectively engage the target tissue by clamping the tissue between opposite gripping portions on each of the jaws. As indicated by the arrow HH shown in FIG. 9B, the first jaw 5462 and the second jaw 5482 are movable with respect to each other for moving between an open orientation (not shown), which can be similar to the open orientation shown in FIG. 6A for the instrument 3500, and the closed orientations shown in FIGS. 8, 9A and 9B. The second proximal needle alignment portion 5491 of the second jaw 5482 is located opposite to, and aligned with, the first proximal needle alignment portion 5471 when the first and the second jaws are a closed orientation, such as the closed orientations shown in FIGS. 9A and 9B. As discussed in greater detail below, the needle alignment portions can be configured for self-righting needle functions when the first and second jaws are moving from an open to closed orientations, as well as for needle clamping for suturing.

Referring to FIG. 11A, the first proximal needle alignment portion 5471 and the second proximal needle alignment portion 5491 are configured to receive a curved portion 5011 of a needle 5010 between the first and second proximal needle alignment portions 5471, 5491 when the first and second jaws 5462 and 5482 are in the open orientation (not shown). The first proximal needle alignment portion 5471 and second proximal needle alignment portion 5485 define a clamp path 5476 therebetween when the first and second jaws 5462 and 5482 are in the closed orientation. The curved portion 5011 of the needle 5010 can be received between the first and second proximal needle alignment portions 5471, 5491 when the first and the second jaws 5462, 5482 are in an open orientation, in which the curved portion is not limited to having a particular alignment when inserted and received. The first and second proximal needle alignment portions 5471, 5491 are configured to engage the curved portion 5011 while the first and second jaws 5462, 5482 move with respect to each other toward the closed orientation and clamp the curved portion 5011 to thereby hold the needle in its pre-configured orientation.

Thus, in a manner similar to the instruments 2400, 3400 and 4400 discussed above, the instrument 5400 can function as a self-righting needle holder in which a needle 5010 can be quickly and easily received, self-aligned and clamped into a pre-configured needle driver orientation with respect to the instrument for performing suturing functions. In addition, the instrument 5400 can be used to engage tissue via its contact portions 5463, 5483 for performing other surgical functions, such as gripping, cutting or cauterizing the tissue. The combinations of functionalities can be provided by the contact portions 5463, 5483 and the needle alignment portions 5464, 5484, which benefits are further enhanced by the ranges of movements provided by the wrist mechanism arrangement of the instrument 5400. Thus, instrument 5400 is configured to provide a wide range of surgical functions including engaging tissue via its contact portions and suturing via its needle alignment portions within wide ranges of motion, as well as quickly changing between surgical functions which doing so.

Referring to FIG. 11A, the clamp path 5476 that is defined between the first and second proximal needle alignment portions 5471, 5491 has a radius of curvature, $R_{ClampPath}$, which corresponds to the needle radius of curvature, $R_{Needle}$, at the curved portion 5011 of the needle. In some embodiments, the radius of curvature $R_{ClampPath}$ is equal to the needle radius of curvature $R_{Needle}$. When the needle 5010 is retained within the clamp path 5476 and while the second jaw is in the closed orientation shown in FIGS. 9A and 9B, the curved portion 5011 of the needle 5010 aligns with radius of curvature of the clamp path 5476. In this manner, a center $C_{RN}$ of the radius of curvature, $R_{Needle}$, of the needle 5010 is guided by the first and second proximal needle alignment portions when clamping the curved portion of the needle 5010 within the clamp path 5476. In some embodiments, the clamp path radius of curvature $R_{ClampPath}$ is larger or smaller than the needle radius of curvature $R_{Needle}$ such that the instrument can hold needles of different sizes and varying curvatures in accordance with surgical requirements while still self-guiding the needle into the desired alignment and orientation in the instrument. Whether the clamp path has the same radius of curvature, $R_{ClampPath}$, or a radius that is larger or smaller than the needle radius of curvature $R_{Needle}$, the clamp path radius of curvature $R_{ClampPath}$ nonetheless includes a sufficient number of needle contact points to define the curved clamp path, engage the curved portion 5011 of the needle, and guide it into the orientation shown in FIGS. 9A and 9B.

As shown by the arrows HH in FIGS. 9A and 9B, when the second jaw 5482 moves to the closed orientation and clamps the needle between the jaws, it rotates the needle 5010 relative to the jaws such that the center $C_{RN}$ of the radius of curvature, $R_{Needle}$, is located at a pre-determined orientation with respect to the first and second jaws. In particular, as shown in FIG. 11A, the center $C_{RN}$ of the radius of curvature, $R_{Needle}$, is coincident with the center $C_{CP}$ of the radius of curvature $R_{ClampPath}$ of the clamp path 5476. In particular, as shown in FIG. 11A, the center $C_{RN}$ of the radius of curvature, $R_{Needle}$, becomes coincident with the center $C_{CP}$ of the radius of curvature $R_{ClampPath}$ of the clamp path 5476 such that an apex, AP, of the curved needle portion 5011 matches an apex of the proximal clamp path 5476. The pre-determined orientation can be a desired orientation with respect to the instrument 5400 for performing suturing functions. For example, as shown in FIG. 9B, in some embodiments, the pre-determined orientation of the center $C_{CP}$ of the radius of curvature $R_{ClampPath}$ of the clamp path 5476 (and thus, the center $C_{RN}$ of the radius of curvature, $R_{Needle}$) intersects a longitudinal axis of the first jaw 5462 and the second jaw 5482 at the first and second proximal needle alignment portions 5471, 5491 at an angle of about ninety degrees. In other embodiments, however, the radius of curvature $R_{ClampPath}$ of the clamp path 5476 intersects a longitudinal axis of the first jaw 5462 and the second jaw 5482 at the first and second proximal needle alignment portions 5471, 5491 at any suitable angle.

Thus, the first and second proximal needle alignment portions 5471 and 5491 cooperate to self-align the needle while moving the first and second jaws 5462 and 5482 into a clamped arrangement for suturing functions. As such, when the first and second jaws 5462 and 5482 move from the open orientation (not shown) to the closed orientation shown in FIGS. 9A and 9B, and while the curved portion 5011 of the needle is located between the first and second proximal needle alignment portions 5471, 5491, the first and second proximal alignment portions of the jaws are configured to engage the curved portion 5011 of the needle to rotate the needle 5010. These needle alignment portions do so by clamping the curved portion 5011 of the needle, such that the curved portion of the needle aligns with radius of curvature of the clamp path 5476. In this manner, a needle 5010 can be readily clamped in place between the jaws of the instrument 5400 into a secure needle-driver, suturing arrangement with the instrument, such that the instrument can be manipulated to drive the needle 5010 while the needle is securely clamped to the instrument and retained in a desired pre-configured orientation for performing suturing functions. The aligned curvatures between the needle and the clamp path 5476 while the needle 5010 is retained in this clamped arrangement cooperate to firmly retain and orient the needle with respect to the instrument.

Figure 11C:
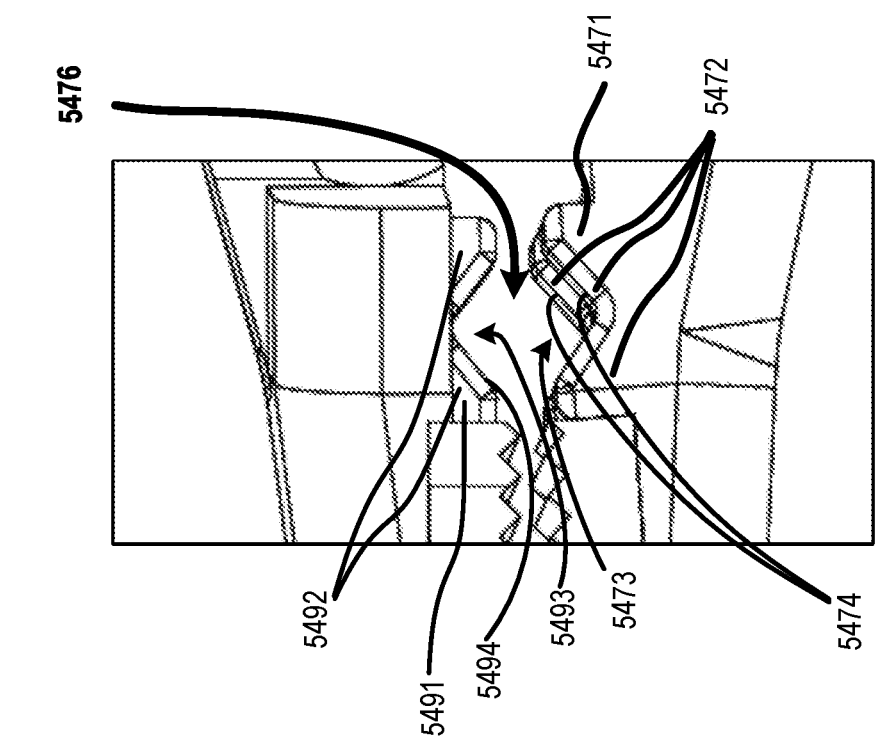
FIG. 11C is a close view of the area identified as region L shown in FIG. 9B.
Figure 11B:
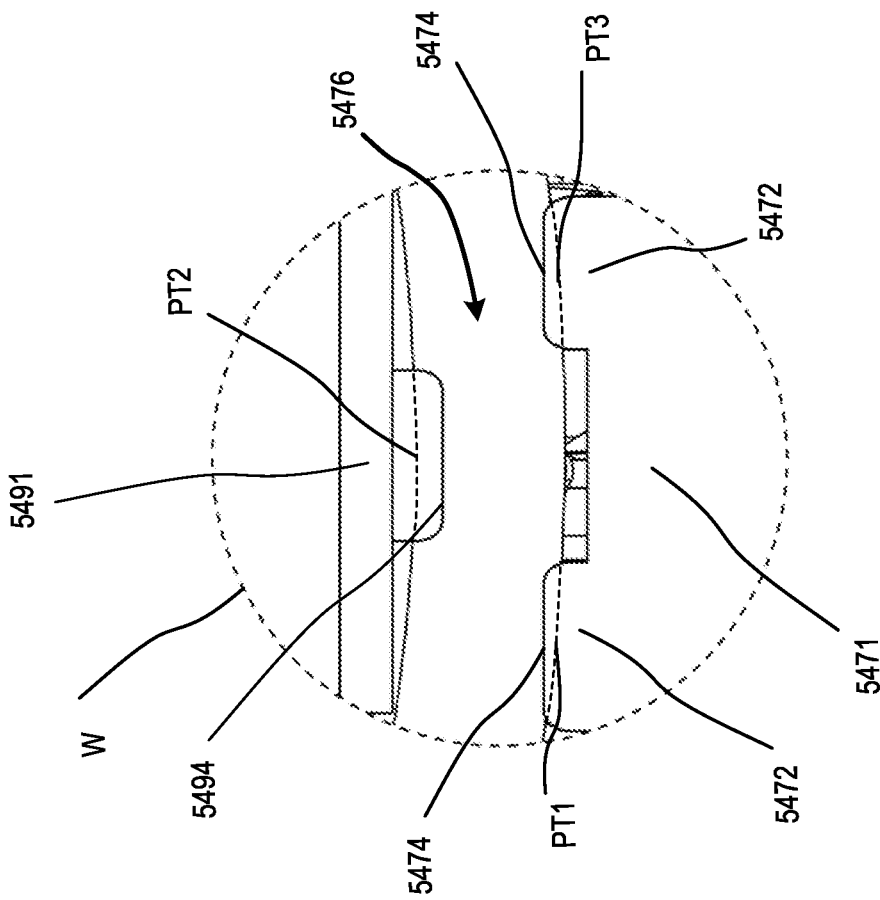
FIG. 11B is a close view of the area identified as region W shown in FIG. 11A.

Referring now to FIGS. 11B and 11C, the first proximal needle alignment portion 5471 on the first jaw 5462 can include a pair of clamp supports 5472 that are laterally spaced apart from each other across the width of the first jaw 5462, such that one of the pair of clamp supports 5472 is located at each side of the first jaw, and a gap is defined between the clamp supports. Each of the pair of clamp supports 5472 includes a clamp surface 5474 that is offset from the first jaw 5462 toward the second jaw 5482 when in the closed orientation. As such, the pair of clamp supports 5472 together provide a raised support platform with the respect to the gap that is defined between the clamp supports. The second proximal needle alignment portion 5491 on the second jaw 5482 can be located opposite from and aligned with the first proximal needle alignment portion 5471 when the first and second jaws are in the closed orientation. The second proximal needle alignment portion 5491 includes a central clamp support 5492 that is centered laterally across the width of the second jaw 5482, such that it is located opposite from and aligned with the gap between the clamp supports 5472 when the first and second jaws are in the closed orientation. The central clamp support also includes a support surface 5494, which when in the closed orientation, is oriented in an opposite direction from the support surfaces 5474 of the pair of clamp supports 5472 and is aligned with the gap formed by the lateral offset between the pair of clamp supports. The support surface 5494 is also offset in a similar, yet opposite manner than the pair of clamp supports, such that the support surface 5494 of the central clamp extends away from the second jaw and toward the first jaw when the first and second jaws are in the closed orientation.

Thus, as shown in FIG. 11B, the pair of laterally spaced support surfaces 5474 of the pair of clamp supports 5472 that extend away from the first jaw 5462 can cooperate with the laterally centered support surface 5494 of the central clamp support 5492 that extends away from the second jaw 5482 to define a curved clamp path 5476 extending widthwise across the first and second jaws 5462, 5482 when the first and second jaws are in the closed orientation. Further, each of the clamp surfaces on the pair of clamp supports includes at least one point of contact, PT1 and PT3, and the clamp surface on the central clamp support includes at least one point of contact PT2, that can engage the curved portion 5011 of the needle 5010 and form a contact point therewith during self-righting and clamping functions. Thus, the instrument 5400 is configured such that the contact points PT1-PT3 can engage the bend portion 5011 of the needle 5010 while the jaws are moving from the open to the closed orientation after the needle is inserted to place the bend portion 5011 between the jaws while in the open orientation. The contact points PT1-PT3 of the support surfaces engage and clamp on the bend portion 5011 when the first and second jaws move from the open to the closed orientation as discussed above along with FIG. 11A to perform self-righting functions along with clamping the needle.

The support surfaces 5474 and 5494 of the clamp supports can have any appropriate configuration for defining the clamp path 5476, performing the self-driving functions, and clamping the needle 5010 during suturing. In some embodiments, one or more of the support surfaces can define a depression 5473, 5493 as shown in FIG. 11C, which can enhance the stability of operation for the self-righting functions, and increase hold strength when clamping the needle. In some embodiments, the depression 5473, 5493 can form a notch in the clamp support. In some embodiments (not shown), one or more of the support surfaces can be angled to improve further the amount and size of contact between the clamp supports and the bend portion 5011. In other embodiments, the clamp surfaces can include combinations of orientations to increase retention of the needle during suturing and provide additional options for clamping the needle 5010, such as combinations of options including angled surfaces, peaked surfaces and/or surfaces forming depressions.

For example, FIGS. 12, 13, 14A and 14B show an instrument 6400, which can provide multiple options for needle alignment orientations, needle clamping strengths, needle holding locations, and the amount of needle alignment portions located on a single instrument. The instrument 6400 includes certain aspects, preferences and features as are described above along with instruments 2400, 3400, 4400, and 5400, except as described herein. Like numbers described herein for FIGS. 5A-11C refer to like features of FIGS. 12-14B. Instrument 6400 shown in FIGS. 12-14B differs from instruments described above by providing a combined functionality gripping and needle alignment portion 6471 that can be used for tissue engaging functions including tissue grabbing functions. In addition, the needle alignment portion 6471 can be used for needle alignment functions including self-righting needle functions, needle clamping, and suturing functions. In addition, the needle alignment portion 6471 can provide multiple needle clamping along its length as appropriate for its usage and based on the surgical environment. Thus, instrument 6400 can provide a highly versatile tool that can be used to provide many different tissue-engaging functions including grabbing, cutting, moving or otherwise surgically manipulating tissue. In addition, instrument 6400 can quickly and easily allow a needle to be installed along multiple locations of the instrument, self-righted and clamped, and used for suturing.

Figure 12:
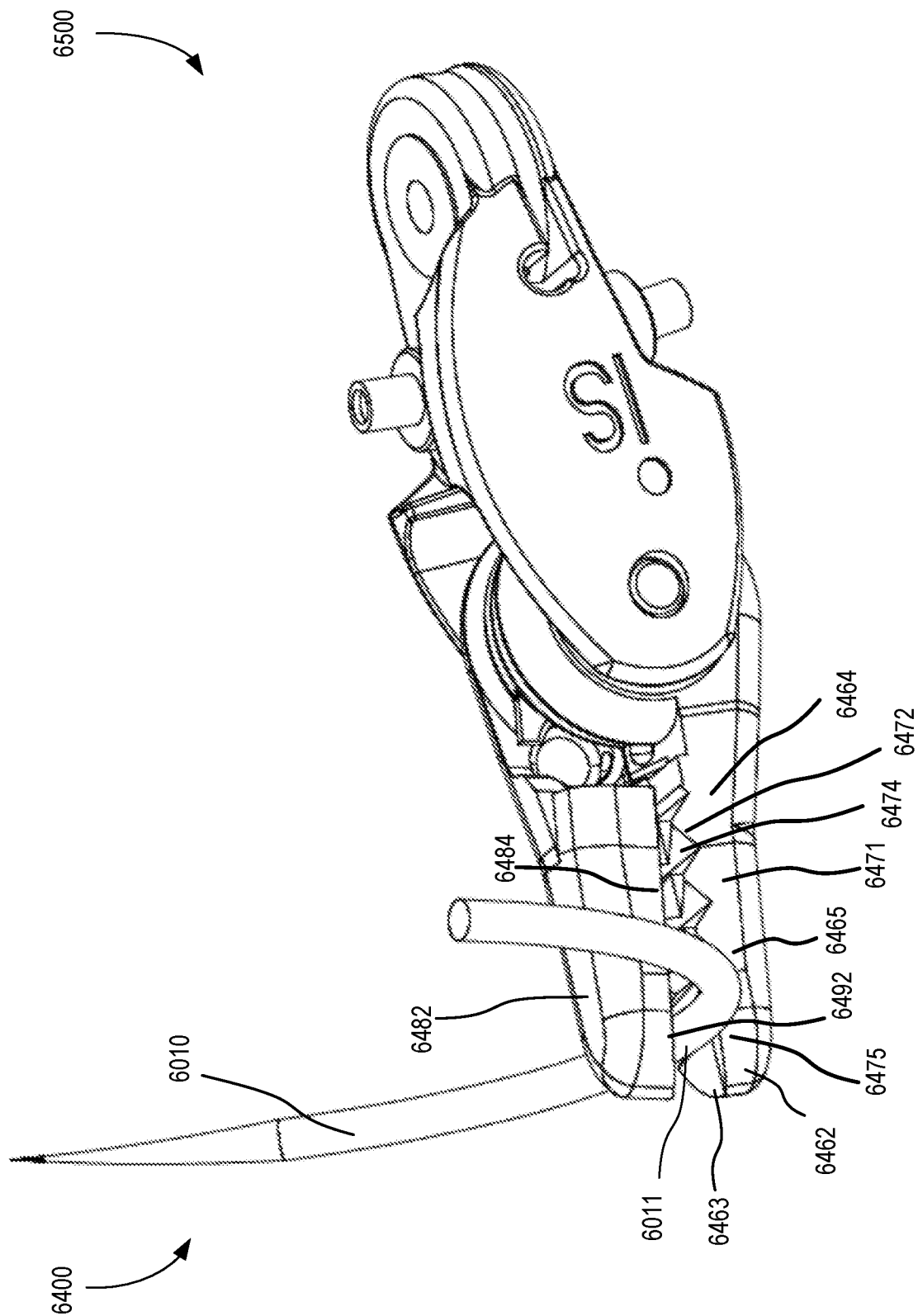
FIG. 12 is an enlarged, side perspective view of a distal end portion of an instrument, according to an embodiment, shown in a first, closed orientation clamping a needle between the instrument jaws, in which the first link and smaller components, such as the idler pulleys and tension members, have been removed for clarity.
Figure 13:
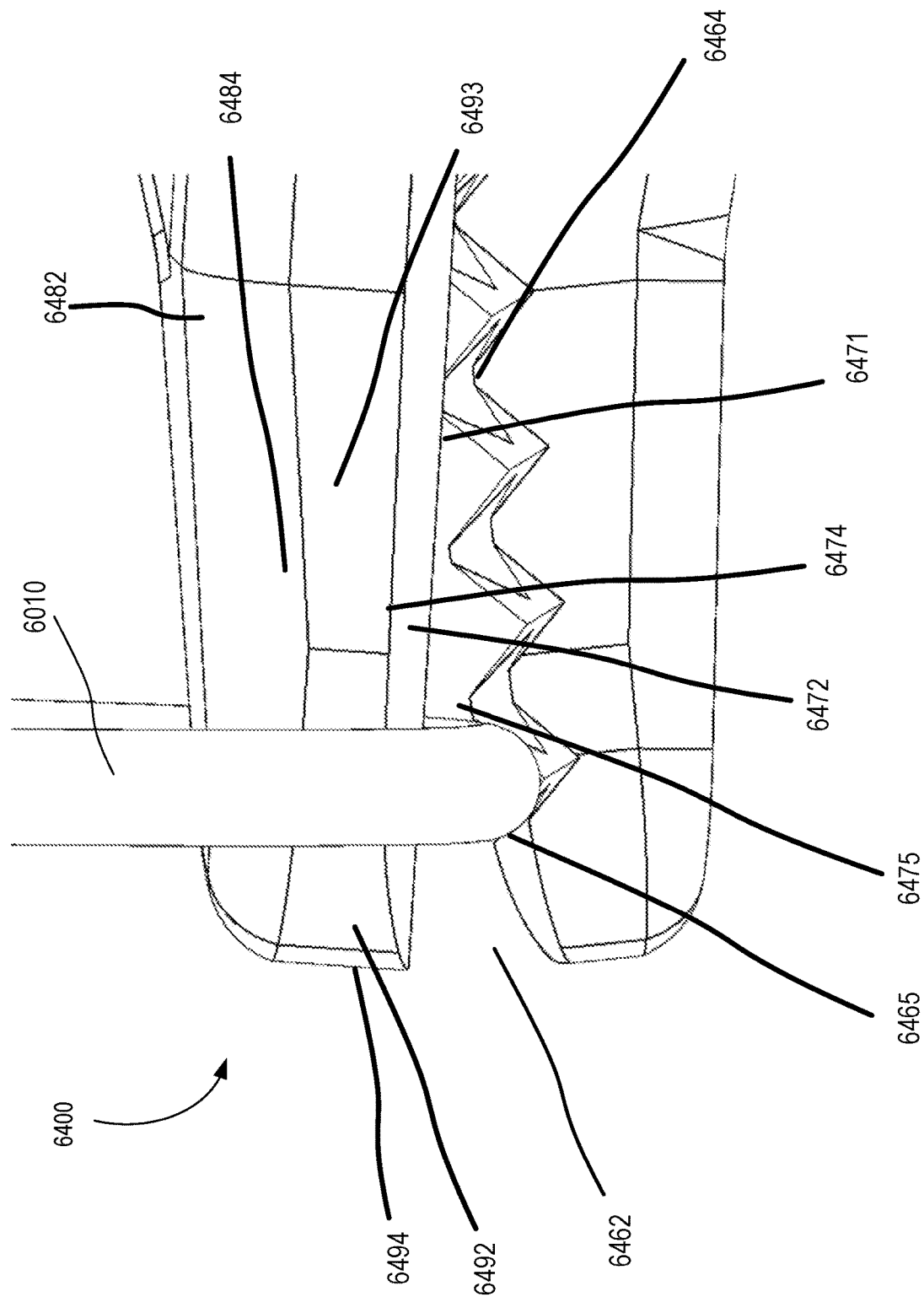
FIG. 13 is an enlarged side view of the distal end portion of the instrument shown in FIG. 12.
Figure 14:
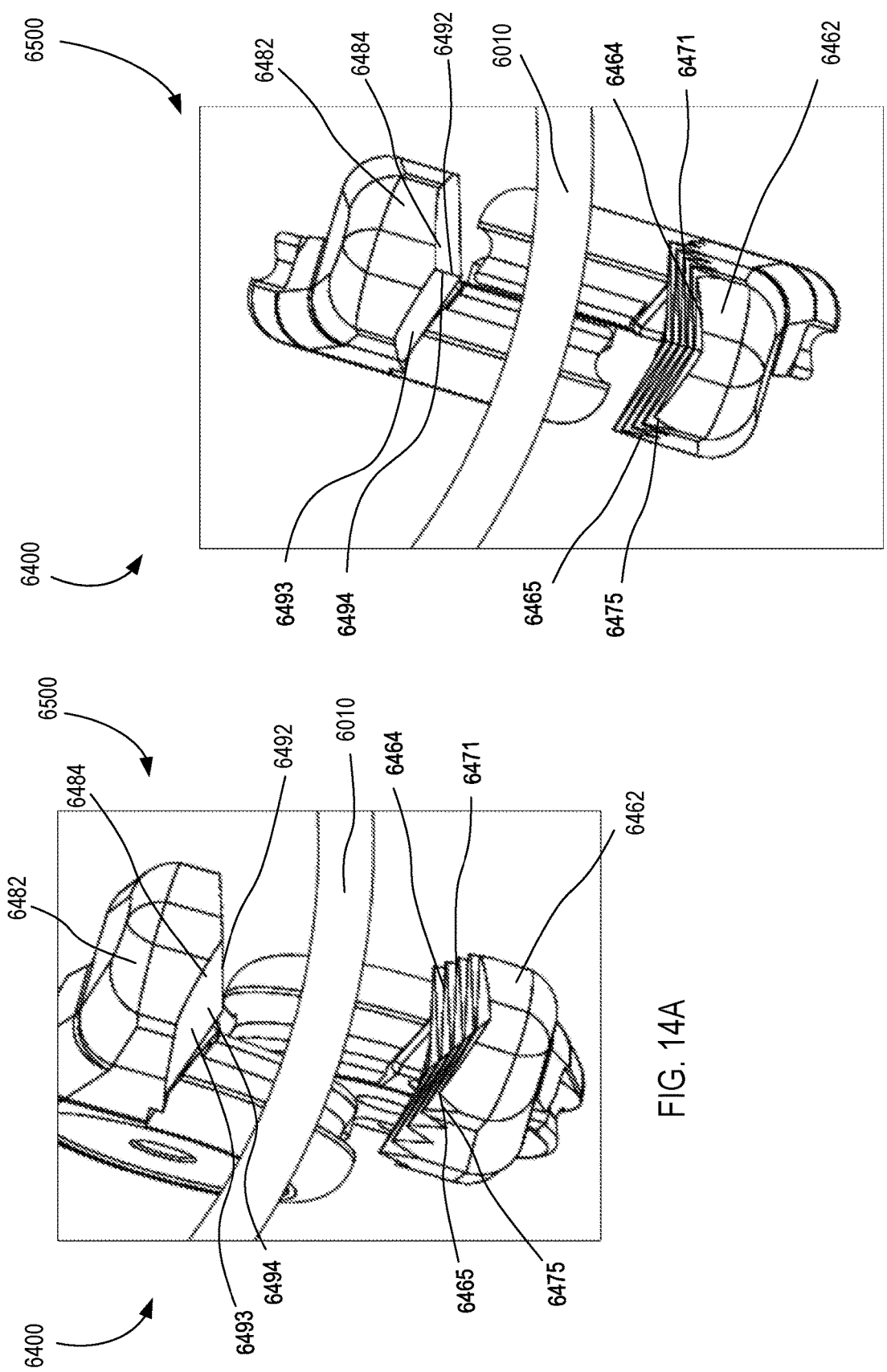
FIGS. 14A and 14B are perspective views of the distal end portion of the instrument of FIG. 12 shown in partially exploded views.

Referring to FIGS. 12 and 13, the first jaw 6462 includes a first proximal gripping portion 6464 and a first distal gripping portion 6465, as well as a first proximal needle alignment portion 6471, and a first distal needle alignment portion 6475. In addition, the second jaw 6482 includes a second gripping portion 6484 extending longitudinally along the jaw, which includes a central clamp support 6492 having a pair of angled surfaces 6493 that extend along each side of a peak 6494. The first proximal needle alignment portion is disposed along the first jaw in a manner similar to the first proximal needle alignment portion 5471 discussed above along with FIGS. 9B-11C except for the angular, sloped shape of the pair of clamp supports 6472 that can provide enhanced clamping and engagement. However, the first jaw 6462 further includes a plurality of needle alignment portions that are formed in series in the longitudinal direction of the first jaw extending from the first proximal needle alignment portion 6471 to the first distal needle alignment portion 6475 located at the distal end portion 6463 of the first jaw. Thus, as shown in FIG. 12, the first distal needle alignment portion 6475 includes at least two pairs of clamp supports 6472 arranged in series adjacent to each other and formed in series in a distal direction along the longitudinal axis of the first jaw. The first distal needle alignment portion 6465 includes pairs of clamp supports 6472 that are also arranged in series in the longitudinal direction along the first jaw as in the first proximal needle alignment portion 6464.

Referring to FIG. 12, the first proximal gripping portion 6464 and the first distal gripping portion 6465 also include the series of pairs of spaced apart clamp supports 6472 that extend in the longitudinal direction along the first jaw for the needle alignment portions. The series of lateral peaks from the pairs of clamp supports 6472, as well as the V-shaped depression defined between each pair of the clamp supports, forms the gripping portions 6464 and 6465 as well as the needle alignment portions.

Thus, the first jaw 6462 is configured as a single, integrated arrangement of needle alignment portions that also form the gripping portions. The laterally peaked, V-shaped pairs of clamp supports arranged in series provide a tooth-like shape along the first jaw, which enhances the grip between target tissue (not shown) and the tooth-like surface of the first jaw 6462. Further, the series of clamp supports that are arranged along the first jaw provide multiple needle alignment portions in the longitudinal direction of the first jaw from the first proximal portion 6464 to the distal end 6465, in which a needle 6010 could be clamped for suturing.

Each of the pairs of clamp supports 6472 include a clamp surface 6474 that defines a V-shaped depression between the lateral, outer portion of each of the pairs of clamp supports 6472. In addition, each of the clamp supports 6472 for a pair of clamp supports the laterally slopes from the lateral edge portions of the first jaw 6462 to the center the V-shaped depression, which is located at longitudinal center of the first jaw as shown in FIGS. 14A and 14B. The V-shape of the depression defined by the clamp supports 6472 better matches the curvature of the curved needle portion 6011, which can provide for larger sized points of contact between the clamp surfaces 6474 and the needle during self-righting functions and when holding the needle during suturing.

Figure 15:
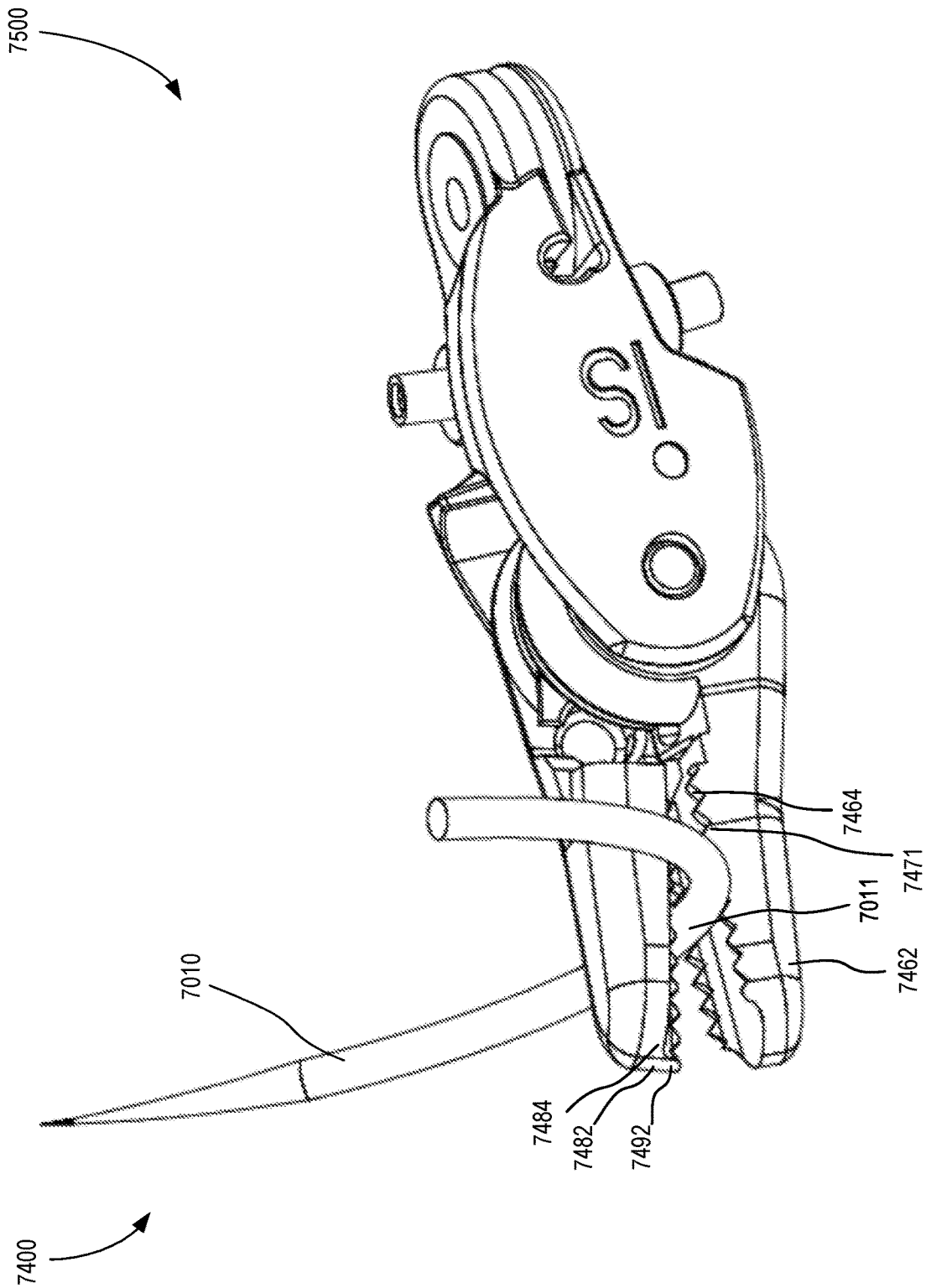
FIG. 15 is an enlarged, side perspective view of a distal end portion of an instrument, according to an embodiment, shown in a first, closed orientation clamping a needle between the instrument jaws, in which the first link and smaller components, such as the idler pulleys and tension members have been removed for clarity.

The second jaw 6482 includes a single gripping portion 6484 that is formed as a central peak 6492 and a corresponding pair of angled lateral surfaces 6494 disposed on each side of the peak 6492, which extends along the longitudinal length of the second jaw 6482. As such, the second jaw 6482 also provides a single, integrated gripping portion 6484 and needle alignment portion 6492 along its length, which allows for gripping functions or needle clamping function to be performed at multiple locations along the second jaw 6482. Thus, the first jaw 6462 and the second jaw 6482 provide a highly flexible instrument that can perform gripping functions, and needle righting and clamping functions at multiple locations along its length. Instrument 6400 provides combined, multi-functional portions along its length using peaked and angled surfaces formed on both the first and second jaw. In other embodiments, combined, multi-functional portion can be provided along the length of the instrument based on other combinations of features along the length of the jaws. For example, FIGS. 15-16B shown an instrument 7400 that also provides combined gripping functionality and self-righting needle functionality along the length of its first and second jaws. The instrument 7400 includes certain aspects, preferences and features as are described above along with other instruments including instrument 6400, except as described herein. Like numbers described herein previously refer to like features of FIGS. 15-16B.

Instrument 7400 shown in FIGS. 15-16B differs from instruments described above and, in particular, from instrument 6400 by providing a combined functionality gripping portion 7464 that is integrated with a needle alignment portion 7471 that can be used for needle self-alignment and clamping, along the length of the first jaw 7462 and the second jaw as discussed below. Instrument provides this combined, integrated functionality via series of pairs of spaced apart clamp supports 7471 in each of the pairs of supports are disposed along lateral edge portions of the first jaw 7462, which is similar to the arrangement of instrument 6400. However, instrument 7400 makes use of smaller, tooth shaped clamp supports without forming a depression or similar structure to form a clamp path between the pairs of clamp supports 7471 or to engage the curved portion 7011 of the needle. Similarly, the second jaw 7482 includes a peak arrangement for a gripping portion 7484 having a peak that extends along its length, which likewise includes a series of small teeth that correspond with the series of teeth formed along the first jaw 7462.

The tooth-shaped features extending along the lateral portions of the first jaw 7462 and along the peak 7492 of the first jaw are configured to engage the curved portion of the needle 7011 at least three contact portions in a manner similar, for example, with the three contact points discussed along with FIG. 11B above and instrument 5400. However, the arrangement of small teeth for instrument 7400 provide an arrangement of stress concentrating features, which improve the clamping force and amount of engagement between each of the teeth and the needle 7010. Thus, instrument 7400 can provide a highly versatile tool that can be used to provide tissue engaging functions and needle self-righting and clamping functions along the length of its jaws, and to do so with enhanced levels of engagement and retention force between the jaws and the needle.

Figure 17:
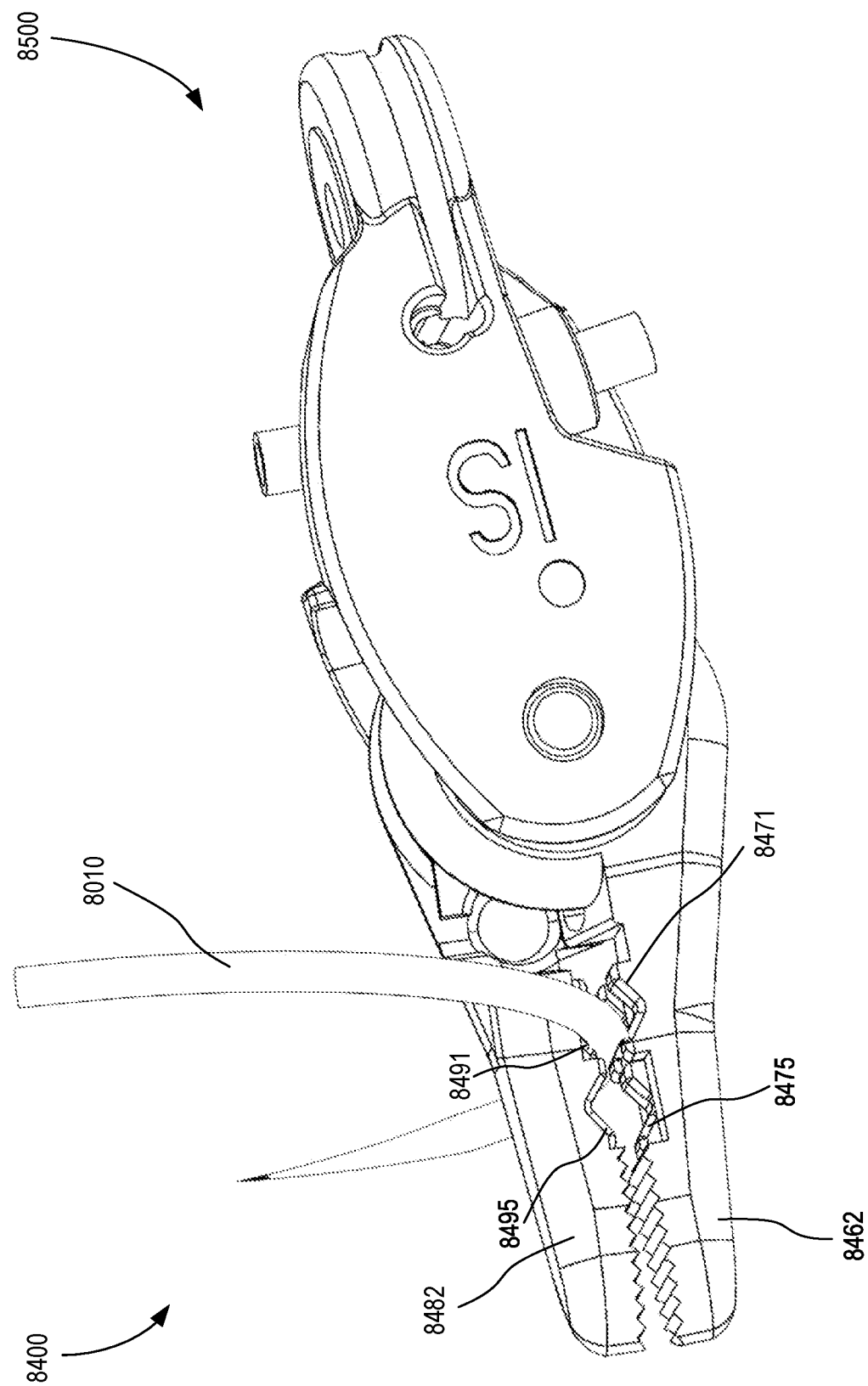
FIG. 17 is an enlarged, side perspective view of a distal end portion of an instrument, according to an embodiment, shown in a first, closed orientation clamping an example needle between the instrument jaws, in which the first link and smaller components, such as the idler pulleys and tension members, have been removed for clarity.
Figure 18B:
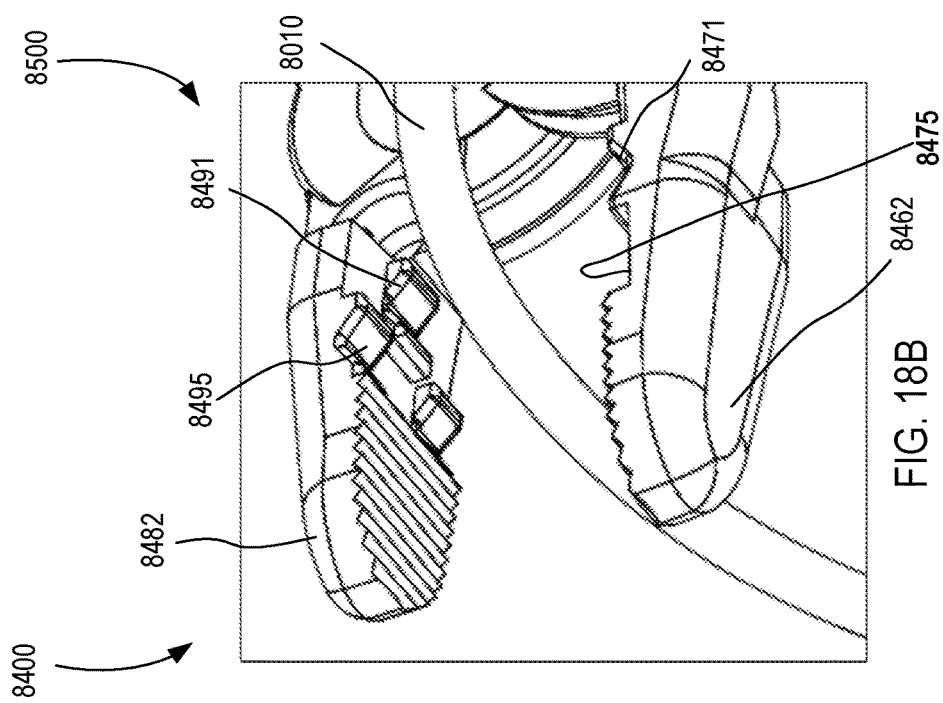
FIGS. 18A and 18B are perspective views of the distal end portion of the instrument of FIG. 17.
Figure 18A:
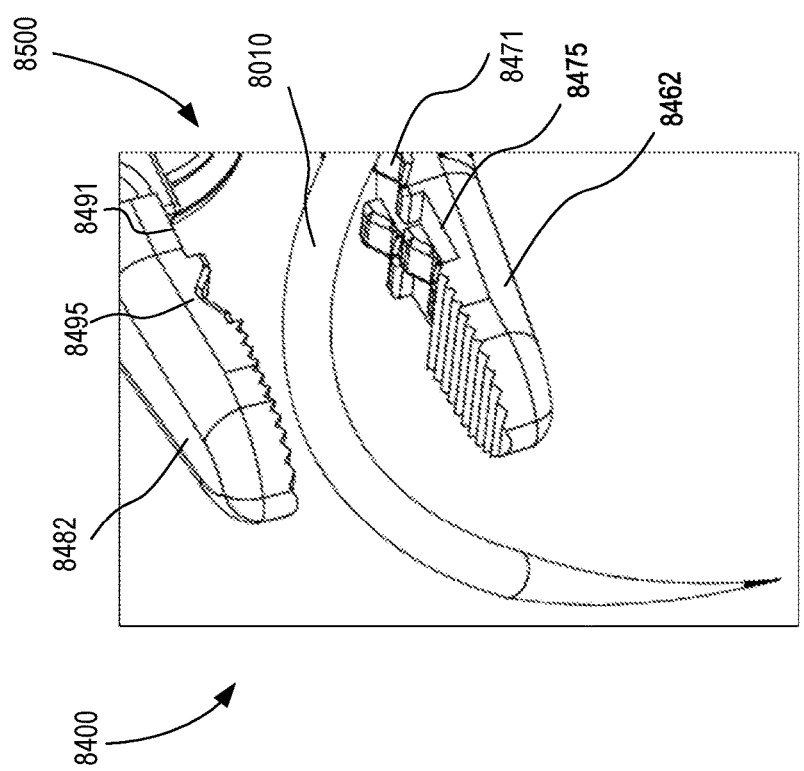

Referring now to FIGS. 17, 18A and 18B, an instrument 8400 is shown, which is similar to instrument 5400 described above and that generally includes the same preferences and features as described above along with instrument 5400 except as described hereafter. Accordingly, like numbers refer to like features described above. In particular, instrument 8400 can be arranged as an option with respect to instrument 5400, which can be modified to include to expand its proximal needle alignment portion 8471, 8491 from a single proximal needle alignment portion defined by the first 8462 and second jaws 8482, to two needle alignment portions 8471, 8491 and 8475, 8495 disposed adjacent to one another in the longitudinal direction of the jaws. Such an optional modification provides the advantages of instrument 5400 described above, along with expanding its functionality to include more than one needle alignment portion.

Further, in a manner similar to the dual needle alignment arrangement described above along with instrument 3400 and FIGS. 6A-6D, the expanded arrangement of instrument 8400 can be configured to provide two different orientations for the needle 8010. As shown in FIG. 17 vs. FIGS. 18A and 18B, the orientation of the needle when clamped between the jaws for suturing can be in an orientation similar to the orientation of instrument 5400 that is shown in FIG. 17. In addition, the needle can be retained in an opposite orientation as shown in FIGS. 18A and 18B, which can provide advantages according to the surgical environment and further enhances the versatility of the instrument 8400.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the instruments described herein (and the components therein) are optionally parts of a surgical assembly that performs minimally invasive surgical procedures, and which can include a patient-side cart, a series of kinematic linkages, a series of cannulas, or the like. Thus, any of the instruments described herein can be used in any suitable surgical system, such as the MIRS system 1000 shown and described above. Moreover, any of the instruments shown and described herein can be used to manipulate target tissue during a surgical procedure. Such target tissue can be cancer cells, tumor cells, lesions, vascular occlusions, thrombosis, calculi, uterine fibroids, bone metastases, adenomyosis, or any other bodily tissue. The presented examples of target tissue are not an exhaustive list. Moreover, a target structure can also include an artificial substance (or non-tissue) within or associated with a body, such as for example, a stent, a portion of an artificial tube, a fastener within the body or the like.

For example, any of the jaws can be constructed from any material, such as medical grade stainless steel, nickel alloys, titanium alloys, or the like. Further, any of the links, jaws, tension members, or components described herein can be constructed from multiple pieces that are later joined together. For example, in some embodiments, a link can be constructed by joining together separately constructed components. In other embodiments, however, any of the links, jaws, tension members, or components described herein can be monolithically constructed.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

What is claimed is:

1. An apparatus, comprising:
   a clevis;
   a first jaw coupled to the clevis, the first jaw comprising a first distal needle alignment portion and a first proximal needle alignment portion, and
   a second jaw coupled to the clevis, the second jaw comprising a second distal needle alignment portion and a second proximal needle alignment portion;
   wherein:
   the second jaw and the first jaw are movable relative to each other between an open orientation and a closed orientation,
   the second distal needle alignment portion is located opposite and aligned with the first distal needle alignment portion when the first jaw and the second jaw are in the closed orientation,
   the second proximal needle alignment portion is located opposite and aligned with the first proximal needle alignment portion,
   the first and the second distal needle alignment portions are configured to retain a needle in a distal needle orientation when in the closed orientation,
   the first and the second proximal needle alignment portions are configured to retain the needle in a proximal needle orientation when in the closed orientation;
   the first and the second distal needle alignment portions define a distal clamp path when in the closed orientation, the distal clamp path having a distal clamp path radius of curvature,
   the first and the second proximal needle alignment portions define a proximal clamp path when in the closed orientation, the proximal clamp path having a proximal clamp path radius of curvature,
   the distal needle orientation includes an upward orientation configured to retain a curved portion of the needle within a first axial plane intersecting a longitudinal axis of the first and the second jaws when in the closed orientation, the distal clamp path being located within the first axial plane, and a center of the distal clamp path radius of curvature being located on a side of the first jaw opposite from the second jaw within the first axial plane, and
   the proximal needle orientation includes a downward orientation configured to retain the curved portion of the needle within a second axial plane intersecting the longitudinal axis of the first and the second jaws when in the closed orientation, the proximal clamp path being located within the second axial plane, and a center of the proximal clamp path radius of curvature being located on a side of the second jaw opposite from the first jaw within the second axial plane.

2. The apparatus of claim 1, wherein:
   the first axial plane is oriented normal to the longitudinal axis of the first and the second jaws when the first jaw and the second jaw are in the closed orientation; and
   the second axial plane is oriented normal to the longitudinal axis of the first and the second jaws when the first jaw and the second jaw are in the closed orientation.

3. The apparatus of claim 1, wherein the first axial plane defines an acute angle between a distal end portion of the first and the second jaws and the longitudinal axis of the first and the second jaws when the first jaw and the second jaw are in the closed orientation.

4. The apparatus of claim 1, wherein:
   the first and the second distal needle alignment portions are configured to orient the needle when the first and the second jaws move from the open orientation to the closed orientation while the curved portion of the needle is within the distal clamp path; and
   the first and the second distal needle alignment portions clamp on the curved portion of the needle when moving from the open orientation to the closed orientation such that the curved portion of the needle aligns with the radius of curvature of the distal clamp path.

* * * * *